US008066644B2

(12) United States Patent  
Sarkar et al.

(10) Patent No.: US 8,066,644 B2
(45) Date of Patent: Nov. 29, 2011

(54) SYSTEM, METHOD AND DEVICE FOR POSITIONING A TARGET LOCATED WITHIN SOFT TISSUE IN A PATH OF AN INSTRUMENT

(75) Inventors: Nilanjan Sarkar, Brentwood, TN (US); Tarun Kanti Podder, Rochester, NY (US); Vishnu Mallapragada, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 863 days.

(21) Appl. No.: 12/123,247

(22) Filed: May 19, 2008

(65) Prior Publication Data

US 2008/0287827 A1 Nov. 20, 2008

Related U.S. Application Data

(60) Provisional application No. 60/938,605, filed on May 17, 2007, provisional application No. 60/971,745, filed on Sep. 12, 2007.

(51) Int. Cl.
*A61B 8/00* (2006.01)
(52) U.S. Cl. ......... 600/461; 600/427; 600/437; 600/475
(58) Field of Classification Search ........................ None
See application file for complete search history.

(56) References Cited

U.S. PATENT DOCUMENTS

| | | | | |
|---|---|---|---|---|
| 4,515,165 A | * | 5/1985 | Carroll | 600/475 |
| 7,496,398 B2 | * | 2/2009 | Nields et al. | 600/427 |
| 7,731,661 B2 | * | 6/2010 | Salcudean et al. | 600/437 |
| 2005/0119568 A1 | * | 6/2005 | Salcudean et al. | 600/437 |
| 2009/0143674 A1 | * | 6/2009 | Nields et al. | 600/437 |

OTHER PUBLICATIONS

Abolmaesumi, P., S. E. Salcudean, W. Zhu, M. R. Sirouspour, S. P. DiMaio, "Image-guided control of a robot for medical ultrasound," IEEE Transactions on Robotics and Automation, vol. 18, No. 1, Feb. 2002.

Alterovitz, R., K. Goldberg, J. Pouliot, R. Taschereau, I-C. Hsu, "Sensorless planning for medical needle insertion procedures," in Proc. IEEE International Conference on Intelligent Robots and Systems, pp. 3337-3343, Oct. 2003.

Antsaklis, P. J., "A brief introduction to the theory and applications of hybrid systems," in Proc. IEEE Special Issue on Hybrid Systems: Theory and Applications, vol. 88, No. 7, pp. 879-887, 2000.

(Continued)

*Primary Examiner* — Long V. Le
*Assistant Examiner* — Nicholas Evoy
(74) *Attorney, Agent, or Firm* — Stites & Harbison PLLC; Jeffrey Haeberlin

(57) ABSTRACT

A system, method and device for positioning a target located within soft tissue in a path of an instrument inserted into the soft tissue includes: a manipulation system including a plurality of force applicators positioned around the soft tissue containing the target; an image acquisition system including an imaging probe for obtaining data for generating an image of the soft tissue containing the target; a detection means for detecting deflection of the target using the data from the imaging probe; and a control means for actuating the plurality of force applicators to apply forces on the soft tissue in response to a detected deflection of the target to move the target back in line with the path of the instrument. In an exemplary embodiment, the soft tissue is a breast, the imaging probe is an ultrasound imaging probe, and the instrument is a biopsy needle.

20 Claims, 11 Drawing Sheets

OTHER PUBLICATIONS

Antsaklis, P. J., X. D. Koutsoukos, "Hybrid systems: review and recent progress," In Samad, T., editor. Software Enabled Control: Information Technology for Dynamical Systems. NY: Wiley-IEEE; 2003.

Azar, F. S., D. N. Metaxas, M. D. Schnall, "Methods for modeling and predicting mechanical deformations of the breast under external perturbations," Medical image Analysis, vol. 6, pp. 1-27, 2002.

Azar, F. S., D. N. Metaxas, M. D. Schnall, "A finite model of the breast for predicting mechanical deformations during biopsy procedure," in IEEE Workshop on Mathematical Methods in Biomedical Image Analysis, 2000, pp. 38-45.

Cleary, K., M. Freedman, M. Clifford, D. Lindisch, S. Onda, and L. Jiang, "Image-guided robotic delivery system for precise placement of theraputic agents," J. Cont. Release, vol. 74, No. 1, pp. 363-368,2001.

DiMaio, S. P., S. E. Salcudean, "Needle insertion modeling and simulation," IEEE Transactions on Robotics and Automation, vol. 19, No. 4, Oct. 2003.

DiMaio, S. P., S. E. Salcudean, "Needle steering and model-based trajectory planning," in Proc. MICCAI, vol. 2878, LNCS, pp. 33-40, 2003.

Elmore, J. G., K. Armstrong, C. D. Lehman, S. W. Fletcher, "Screening for Breast Cancer," Journal of American Medical Association, vol. 293, No. 10, pp. 1245-1256, Mar. 2005.

Glozman, D., M. Shoham, "Image-guided robotic flexible needle steering," IEEE Transactions on Robotics, vol. 23, No. 3, pp. 459-467, Jun. 2007.

Hong, J., T. Dohi, M. Hashizume, K. Konishi, N. Hata, "An ultrasound driven needle insertion robot for percutaneous cholecystostomy," Physics in Med. and Biol., vol. 39, No. 3, 441-455, 2004.

Krupa, A., G. Fichtinger, G. D. Hager, "Full motion tracking in ultrasound using image speckle information and visual servoing," in Proc. IEEE International Conference on Robotics and Automation, pp. 2458-2464, 2007.

Loser, M. H., N. Navab, "A new robotic system for visually controlled percutaneous interventions under CT fluoroscopy", in Proc. MICCAI, vol. 1935, LNCS, pp. 887-896, 2000.

Mallapragada, V., N. Sarkar, T. Podder, "A Robotic System for Real-time Tumor Manipulation During Image Guided Breast Biopsy," in Proc. IEEE International Conference on Bioinformatics and Bioengineering, pp. 204-210, Oct. 2007.

Mallapragada, V., N. Sarkar, T. Podder, "Robot assisted real-time tumor manipulation for breast biopsy," IEEE Transactions on Robotics; Apr. 2009; 25:2; pp. 316-324.

Mallapragada, V., N. Sarkar, T. Podder, "Autonomous Coordination of imaging and Tumor manipulation for Robot Assisted Breast Biopsy" Proc of 2nd Biennial IEEE/RAS-EMBS International Conference on Biomedical Robotics and Biomechatronics Scottsdale AZ; Oct. 19-22, 2008.

McClamroch, N. H., "Displacement control of flexible structures using electrohydraulic servo-actuators," Journal of Dynamic Systems, Measurement and Control, vol. 107, pp. 34-39, Mar. 1985.

Okazawa, S., R. Ebrahimi, J. Chuang, S. E. Salcudean, R. Rohling, "Hand-held steerable needle device," IEEE/ASME Transactions on Mechatronics, vol. 10, pp. 285-296, Jun. 2005.

Olsson, H., K. J. Astrom, "Friction generated limit cycles", IEEE Transactions on Control Systems Technology, vol. 9, pp. 629-636, Jul. 2001.

Patriciu, A., S. Solomon, L. Kavoussi, and D. Stoianovici, "Robotic kidney and spine percutaneous procedures using a new laser-based CT registration method," in Proc. MICCAI, vol. 2208, LNCS, 2001, pp. 249-257.

Pierrot, F., E. Dombre, E. Degoulange, L. Urbain, P. Caron, S. Boudet, J. Gariepy, J. Megnien, "Hippocrate: A safe robot arm for medical applications with force feedback," Medical Image Analysis, vol. 3, No. 3, pp. 285-300, 1999.

Smith, W. L., K. J. M. Surry, G. R. Mills, D. B. Downy, and A. Fenster, "Three-dimensional ultrasound-guided core needle breast biopsy," Ultrasound Med. Biol., vol. 27, No. 8, pp. 1025-1034, 2001.

Solberg, O. V., F. Lindseth, H. Torp, R. E. Blake, T. A. N. Hernes, "Freehand 3D ultrasound reconstruction algorithms—A review," Ultrasound in Med. and Biol., vol. 33, No. 7, pp. 991-1009, 2007.

Stoianovici, D., L. Whitcomb, J. Anderson, R. Taylor, and L. Kavoussi, "A modular surgical robotic system for image guided percutaneous procedures," in Proc. MICCAI, vol. 1496, LNCS, pp. 404-410, 1998.

Stoianovici, D. et al., "A novel mechanical transmission applied to percutaneous renal access," in Proc. ASME Dynamic Systems Control Division, DSC, vol. 61, 2001, pp. 401-406.3.

Surampudi, B., G. Langari, "A fuzzy cancellation of stick-slip in DC motors", Third International Conference on Industrial Fuzzy Control and Intelligent Systems, pp. 24-20, Dec. 1993.

Tsekos, N. V., J. Shudy, E. Yacoub, P. V. Tsekos, I. G. Koutlas, "Development of a robotic device for MRI-guided interventions in the breast," in Proc. Bioinformatics and Bioengineering Conference, 2001, 201-208.

Vilchis, A., J. Troccaz, P. Cinquin, K. Masuda, F. Pellisier, "A new robot architecture for tele-echography," in IEEE Transactions on Robotics and Automation, vol. 19, No. 5, pp. 922-926, 2003.

Vitrani, M. A., G. Morel, T. Ortmaier, "Automatic Guidance of a surgical instrument with ultrasound based visual servoing," in Proc. IEEE International Conference on Robotics and Automation, pp. 510-515, 2005.

Wada, T., S. Hirai, S. Kawamura, N. Kamiji, "Robust manipulation of deformable objects by a simple PID feedback," in Proc. International Conference on Robotics and Automation, 2001, pp. 85-90.

Wellman, P., "Tactile imaging", PhD dissertation, Division of Engineering and Applied Sciences, Harvard University, MA, 1999.

Wunderbaldinger, P., T. H. Helbich, B. Partik, K. Turetschek, and G. Wolf, "First experience with a newdedicated ultrasound system for computer-guided large-core breast biopsy," Eur. Radiol., vol. 11, No. 12, pp. 2460-2464, Dec. 2001.

Masuda, K., E. Kimura, N. Tateishi, K. Ishihara, "Three-dimensional motion mechanism of ultrasound probe and its application for tele-echography system," in Proc. IEEE/RSJ International Conference on Intelligent Robots and Systems, pp. 1112-1116, 2001.

Mallapragada, V., N. Sarkar, T. Podder, "Robot-Assisted Real-time Tumor Manipulation for Breast Biopsy," 2008 IEEE International Conference on Robotics and Automation Pasadena, CA, May 19-23, 2008.

Mallapragada, V., N. Sarkar, T. Podder, Robot System for Tumor manipulation and Ultrasound Image Guidance during breast biopsy; 30th Annual International IEEE EMBS Conference Vancouver BC CA Aug. 20-24, 2008.

Mallapragada, V., "Towards a Robot Assisted Breast Biopsy System" Dissertation.

* cited by examiner

SYSTEM, METHOD AND DEVICE FOR POSITIONING A TARGET LOCATED WITHIN SOFT TISSUE IN A PATH OF AN INSTRUMENT

CROSS-REFERENCE TO RELATED APPLICATIONS

This application claims the benefit of U.S. Provisional Patent Application No. 60/938,605, filed May 17, 2007, and U.S. Provisional Patent Application No. 60/971,745, filed Sep. 12, 2007, the entire disclosures of which are hereby incorporated by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

TECHNICAL FIELD

The presently-disclosed subject matter relates to systems, methods, and devices for positioning a target located within soft tissue in a path of an instrument, including systems, methods, and devices for performing breast tissue biopsies.

BACKGROUND

Breast cancer is the most common cancer among American women and the second leading cause of cancer death in women. American Cancer Society, 2007 [1]. However, early detection of breast cancer has been proven to reduce mortality by about 20% to 35%. Elmore et al., 2005 [2]. Histopathological examination is considered to be the "gold standard" for definitive diagnosis of cancer but requires tissue samples that are collected through biopsy. Of the two major approaches for breast biopsy, needle biopsy and open excisional biopsy, needle biopsy is the most commonly practiced because it is less traumatic, produces little or no scar, allows quicker recovery, and is less expensive.

Despite many benefits of needle biopsy, there are significant technical challenges concerning accurate steering and precise placement of a biopsy needle at the target in breast tissue. To successfully remove a suspicious small targeted lump (e.g., less than 5 mm in diameter) various issues must be addressed, such as architectural distortion and target deflection during needle insertion and poor maneuverability of the biopsy needle. These issues are even more important when the collection of a large and intact core becomes necessary for histopathological diagnosis. Currently, large core samples are collected using large needles such as a 14-gauge (2.1 mm in diameter) true cutting needle, a 10-gauge (3.4 mm in diameter) vacuum-assisted needle, and other radiofrequency (RF) cutting instruments (EN-BLOC® and RUBICOR®) that increase insertion force significantly.

Although mammography, sonography, and magnetic resonance imaging (MRI) techniques have significantly improved early detection of breast cancer, accurate placement of a biopsy needle at the target location and reliable collection of target tissue remain challenging tasks.

Needle biopsies are guided by either stereotactic mammography, magnetic resonance imaging (MRI) or ultrasound (US) imaging. Sonography is the most widely used imaging technique because of its real-time capability and cost-effectiveness. For a few years three dimensional (3D) US systems have been available, but they are not as widely used as two dimensional (2D) US systems because of their high cost. 3D reconstruction algorithms have also been developed for real-time 3D rendering of a volume with image data acquired using a 2D US probe. Solberg et al., 2007 [3]. Real-time 3D reconstruction uses pixel data from the current US image slice to update the 3D volume. Hence the entire 3D volume cannot be reconstructed in real-time. To overcome this, researchers have developed techniques to extrapolate 3D volume data using 2D image slices. This technique is not applicable to breast biopsies due to the deformation of the breast during needle insertion.

Despite numerous benefits of needle biopsy, however, there are significant challenges concerning accurate steering and precise placement of a biopsy needle at the target (the word target as used herein refers to a tumor, a lesion or just a suspected region of tissue) in breast tissue. First, as the needle is inserted, large tissue deformation causes the target to move away from the line of insertion of the needle. DiMaio et al., 2003 [4]. This may necessitate multiple insertions at the same biopsy site to successfully sample the target. Second, current state-of-the-art US guided biopsy technique is highly dependent on the skill of the surgeon. The surgeon performs this procedure by holding the US probe with two or three fingers of one hand while using the other two or three fingers to stabilize the breast, and inserts the needle with the other hand. Since 2D sonography only provides image of a planar cross-section, if the target moves out of plane of the US probe, the surgeon has to continuously reorient the US probe to keep the needle and the target in the imaging plane while inserting the needle. It is critical to orient the imaging plane parallel to the needle, otherwise a false impression of the needle tip causes sampling errors. Since stabilization of the breast is problematic and steering of the needle inside the breast is extremely difficult, many insertion attempts may be required to successfully sample the target. This may cause architectural damage to the tissue, excessive bleeding obscuring the guiding images, surgeons' fatigue and patient discomfort.

Currently available commercial biopsy instruments (Mammotome®, Vacora® etc.) do not compensate for target movement during needle insertion. Robotic systems to improve the accuracy of needle insertions (see: Stoianovici et al. 1998 [5] and Cleary et al., 2001 [6]) do not provide real-time trajectory correction to overcome error due to target movement. In Okazawa et al., 2005 [7], DiMaio et al., [8] and Glozman et al., 2007 [9], steerable needle techniques are presented that allow steering the tip of the needle towards the target during insertion. Steerable devices can only be used with small caliber needles and hence are unsuitable for core needle biopsies. A visually controlled needle-guiding system is developed in Loser et al., 2000 [10], for automatic or remote controlled percutaneous interventions. Though this system potentially reduces the number of insertions required to sample the target, maneuvering a needle inside the breast causes tissue damage. In Azar et al, 2002 [11] and Alterovitz et al., 2003 [12], a finite element model of the breast is used to predict the movement of the target. The needle path is planned based on this prediction to accurately sample the target. To get an accurate prediction of the movement of the target, finite element analysis requires the geometric model and mechanical properties of the breast. In [11], the average time for computation is 29 minutes.

Researchers have developed robotic systems to alleviate the difficulty associated with acquiring US images during medical procedures. A force controlled robotic manipulator for performing cardiovascular 3D US image acquisition has been presented in Pierrot et al, 1999 [14]. Teleoperated master/slave robotic systems have been developed that enable remote acquisition of US images. See: Masuda et al., 2001 [15] and Vischis et al., 2003 [16]. A needle driver robot is presented in Hong et al., 2004 [17] where two degrees of freedom (DOF) in the US image plane are controlled through visual servoing. In this approach the needle is constrained to lie in the US image plane for visual feedback. This idea is extended in Vitrani et al., 2005 [18], where the controlled instrument is not constrained to lie in a plane but has to intersect with the US image plane. An image guided robot for positioning the US probe and tracking a target in real-time has been developed for diagnostic US Abolmaesumi et al., 2002 [19]. The robot controller, US image processor and the operator have shared control over the robot for guiding the US probe.

Even though these systems greatly reduce the difficulty of acquiring US images, the target cannot be tracked in real-time if it moves out of the imaging plane of the probe. In Krupa et al., 2007 [20], a speckle decorrelation technique is presented for estimating out-of-plane motion of a target. Simulation results presented assume rigid motion of internal tissue to preserve correlation between successive image planes. Due to needle insertion and target manipulation, large tissue deformation occurs inside the breast which prohibits application of this technique.

Force sensors are typically used to ensure contact between the surface and the US probe [14][16][19].

A hybrid controller is needed for coordinating multiple systems for robotic biopsy is needed. There has been some work on developing such hybrid controllers in other non-analogous fields, such as industrial robotics, medicine and manufacturing (see: Antsaklis, 2000 [23]), however no work has been done with respect to such a system for biopsy purposes.

BRIEF SUMMARY OF THE INVENTION

The system, method and device described herein guide a target towards a line of insertion of an instrument, such as a needle, instead of steering the instrument towards the target during insertion. The system, method and device use a target manipulation system that positions the target inline with the instrument during insertion. The real-time target manipulation system presented is a set of position controlled force applicators. These applicators are placed around the soft tissue, such as a breast, during the instrument insertion procedure. They control the position of the target, by applying forces on the surface of the soft tissue, such that the target is always placed inline with the instrument. A PI or PID controller minimizes the tracking error in the position of the target. In this approach, instrument insertion force is treated as a disturbance to the system.

The system, method and device utilize a robust image acquisition system that automatically searches and recovers the target should it go out of a field of view of the imaging probe. A sensorless contact detection technique reliably detects contact transitions based on image data.

To coordinate the target manipulation system and the image acquisition system, a hybrid supervisory controller provides comprehensive assistance during procedures.

The robotic device has the following advantages: (a) success rate of the procedure (as defined by the number of insertions required at a particular site to successfully sample the target) will be increased since the target is accurately positioned inline with the instrument; (b) since instrument alignment, imaging probe positioning, target localization and soft tissue stabilization are automated, it will likely minimize fatigue of the surgeon; (c) since the instrument is not steered inside the soft tissue, and number of insertions reduced, tissue damage is also minimized (patient discomfort is reduced) and the structural integrity of the tissue specimen is preserved; and (d) by improving accuracy of the procedure, it will potentially enhance the diagnostic outcome by reducing false negatives.

Advantageously, in addition to the needle biopsy procedure described herein, the device, system and method of the invention has utility with respect to at least the following additional procedures: ablation; cryotherapy; radioactive seed placement; targeted drug injection; and minimally invasive surgery.

This Summary describes several aspects of the presently-disclosed subject matter, and in many cases lists variations and permutations of these aspects. This Summary is merely exemplary of numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Generally, a system, method and device for positioning a target located within soft tissue in a path of an instrument inserted into the soft tissue includes: a manipulation system including a plurality of force applicators positioned around the soft tissue containing the target; an image acquisition system including an imaging probe for obtaining data for generating an image of the soft tissue containing the target; a detection means for detecting deflection of the target using the data from the imaging probe; and a control means for actuating the plurality of force applicators to apply forces on the soft tissue in response to a detected deflection of the target to move the target back in line with the path of the instrument.

In one aspect of the invention, the imaging probe is mounted on a drive mechanism for moving the imaging probe in at least two dimensions with respect to the soft tissue, and the control means is further for actuating the drive mechanism to move the imaging probe to maintain contact with the soft tissue when a loss of contact between the imaging probe and the soft tissue is detected. Also, the control means actuates the drive mechanism to move the imaging probe to track the target if the target moves out of a field of view of the imaging probe.

In another aspect, the system further includes an instrument guidance device for fixing the path of the instrument. The instrument guidance device may further have an instrument path sensor for measuring a characteristic of the path of the instrument. The control means may utilize the characteristic of the path of the instrument in actuating the plurality of force applicators to place the target in line with the path for insertion of the instrument.

According to yet another aspect, the control means includes a target manipulation system controller for controlling the manipulation system, an image acquisition system controller for controlling the image acquisition system, and a high level supervisory controller for coordinating the target manipulation system controller and the image acquisition system controller based on events. The control means may further include an interface between the high level supervisory controller, and the target manipulation system controller and the image acquisition system controller. The interface is for converting between continuous-time signals and sequences of symbols representing tasks. The high level supervisory controller may further have a process monitoring module for monitoring event information received from the target manipulation system controller and the image acquisition system controller via the interface, and a decision making module for determining tasks to implement in response to the events. The decision making module may further send control commands to the target manipulation system controller and the image acquisition system controller via the interface.

In accord with an important implementation, each of the plurality of force applicators includes an end effector positioned for engaging a surface of the soft tissue, an end effector actuator for effecting movement to the end effector, and an end effector position sensor for sensing a position of the end effector for use by the control means. The drive mechanism for moving the imaging probe may have an imaging probe position sensor for sensing a position of the imaging probe for use by the control means. Further, the instrument guidance device may have an instrument path sensor for sensing a characteristic of the path of the instrument for use by the control means.

In an exemplary embodiment, the soft tissue is a breast, the target is a suspected tumor, the imaging probe is an ultrasound imaging probe, and the instrument is a biopsy needle.

Other features and advantages of the invention with be set forth in, or apparent from, the detailed description of exemplary embodiments of the invention found below.

BRIEF DESCRIPTION OF THE DRAWINGS

FIG. 11 is a graph of the locus of the target of the first experiment;

DETAIL DESCRIPTION OF EXEMPLARY EMBODIMENTS OF THE INVENTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently-disclosed subject matter includes a system, method and device for positioning a target located within soft tissue in a path of an instrument.

Figure 1A:
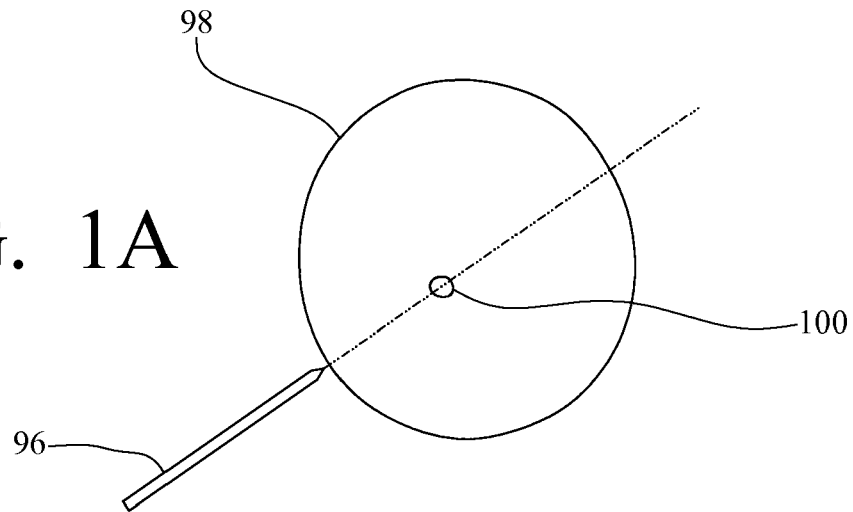
FIG. 1A, FIG. 1B, and FIG. 1C are a schematic views of a needle insertion in an image guided breast biopsy.
Figure 1B:
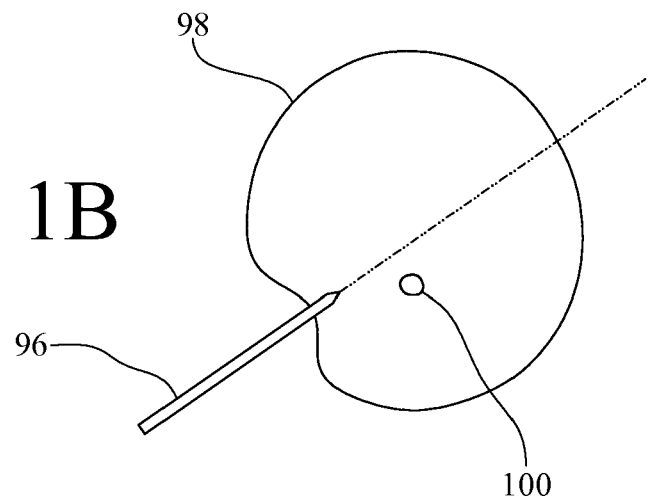
Figure 1C:
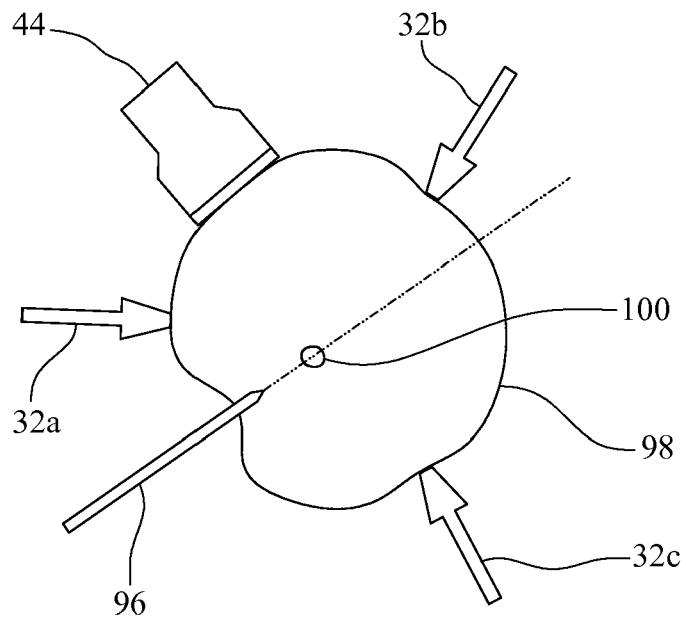

In some embodiments, the target can be a suspected tumor and the instrument can be a biopsy needle, e.g., a breast biopsy. For examples, during an image-guided breast biopsy the subject can lie prone with the breast placed in an opening on a biopsy table. The clinician then inserts a biopsy needle either directly into the biopsy site or through an incision to remove a target sample (e.g., a suspected tumor or portion thereof). With reference to FIG. 1A-FIG. 1C, the two-dimensional plane of the figures represent a horizontal plane passing through the target 100. Because breast tissue is inhomogeneous and its biomechanical properties are nonlinear, if the tip of a needle 96 reaches the interface between two different types of tissue, its further insertion will push the tissue, instead of piercing it, causing unwanted deformations. These deformations move the target 100 away from its original location, as shown in FIG. 1B. Embodiments of the presently-disclosed subject matter allow the target 100 to be positioned and maintained, and/or repositioned, using force applicators 32a, 32b, 32c. As illustrated in FIG. 1C, these force applicators 32a, 32b, 32c can apply control forces on the surface of the breast 98, positioning the target 100 so that it will be intercepted by the biopsy needle 96.

I. EXEMPLARY SYSTEM FOR MOVING A TARGET WITHIN A BREAST INTO A PATH OF A SURGICAL INSTRUMENT INSERTED INTO THE BREAST

Figure 2:
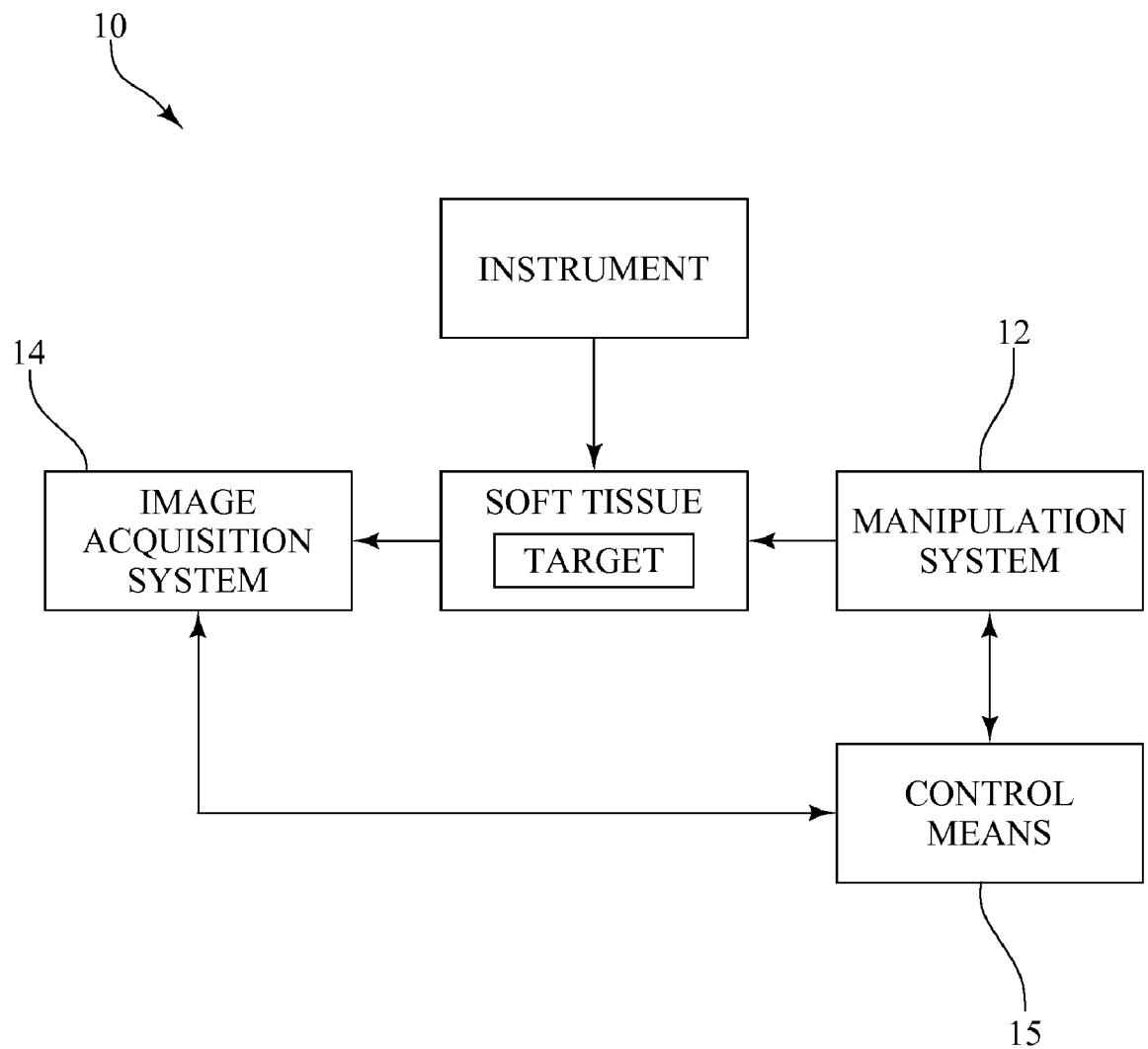
FIG. 2 is a functional block diagram of an exemplary system for positioning a target located within soft tissue in a path of an instrument inserted into the soft tissue.

FIG. 2 shows the components of an exemplary system 10 for positioning, maintaining, or repositioning a target within soft tissue in a path of an instrument inserted into the soft tissue, including a manipulation system 12, an image acquisition system 14, and a control means 15 (i.e. a controller) that serves both detection and control functions. Alternately, the detection function could be performed by a separate detection means, such as a separate data processing device.

For convenience, the description below will discuss exemplary systems, methods and devices for positioning a target located within soft tissue primarily in terms of an exemplary breast biopsy application, but it is understood that no unnecessary limitations are to be read into the scope of the claimed invention because of this exemplary application.

Figure 3:
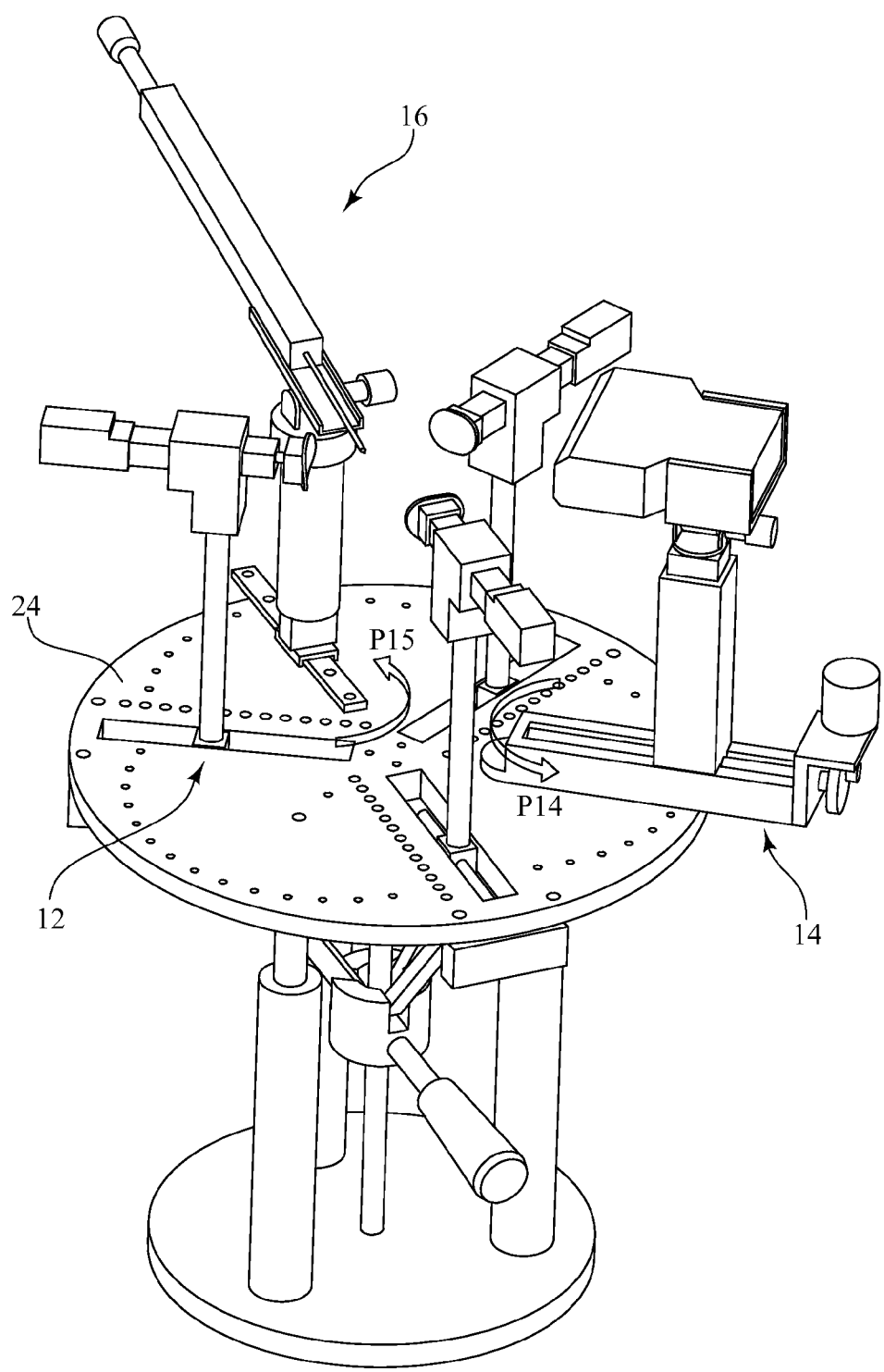
FIG. 3 is a perspective view of an exemplary system for positioning a target located within soft tissue in a path of an instrument inserted into the soft tissue.

FIG. 3 shows an exemplary device for positioning a target located with soft tissue in a path of an instrument inserted into the soft tissue, including a manipulation system 12, an image acquisition system 14, and an instrument guidance device 16, which are described in more detail below. The path of an instrument is fixed by the instrument guidance device 16. Not shown FIG. 3, but described below, is a control means for actuating the manipulation system 12 in response to detecting deflection of the target using target tracking data from the image acquisition system 14 in order to move the target back in line with the path of an instrument.

As described below, in use a soft tissue organ, such as a breast, is received within the manipulation system 12 and imaged by the image acquisition system 14. An instrument, such as a biopsy needle, on the instrument guidance device 16 is inserted in to the breast along an insertion path fixed by the instrument guidance device 16. Deflection of the target is detected by a detection means (shown and described below) using data from the image acquisition system 14, and the control means causes the manipulation system 12 to manipulate the soft tissue organ to move the target back in line with the insertion path for interception by the instrument. The image acquisition system may use stereotactic sensors, a magnetic resonance imager (MRI), an ultrasound (US) sensor, or other known imaging devices, although, as discussed below, aspects of the exemplary system are particularly advantageous for an imaging probe, such as a US sensor, that generates a two-dimensional image corresponding to an imaging plane within the soft tissue organ.

Figure 4:
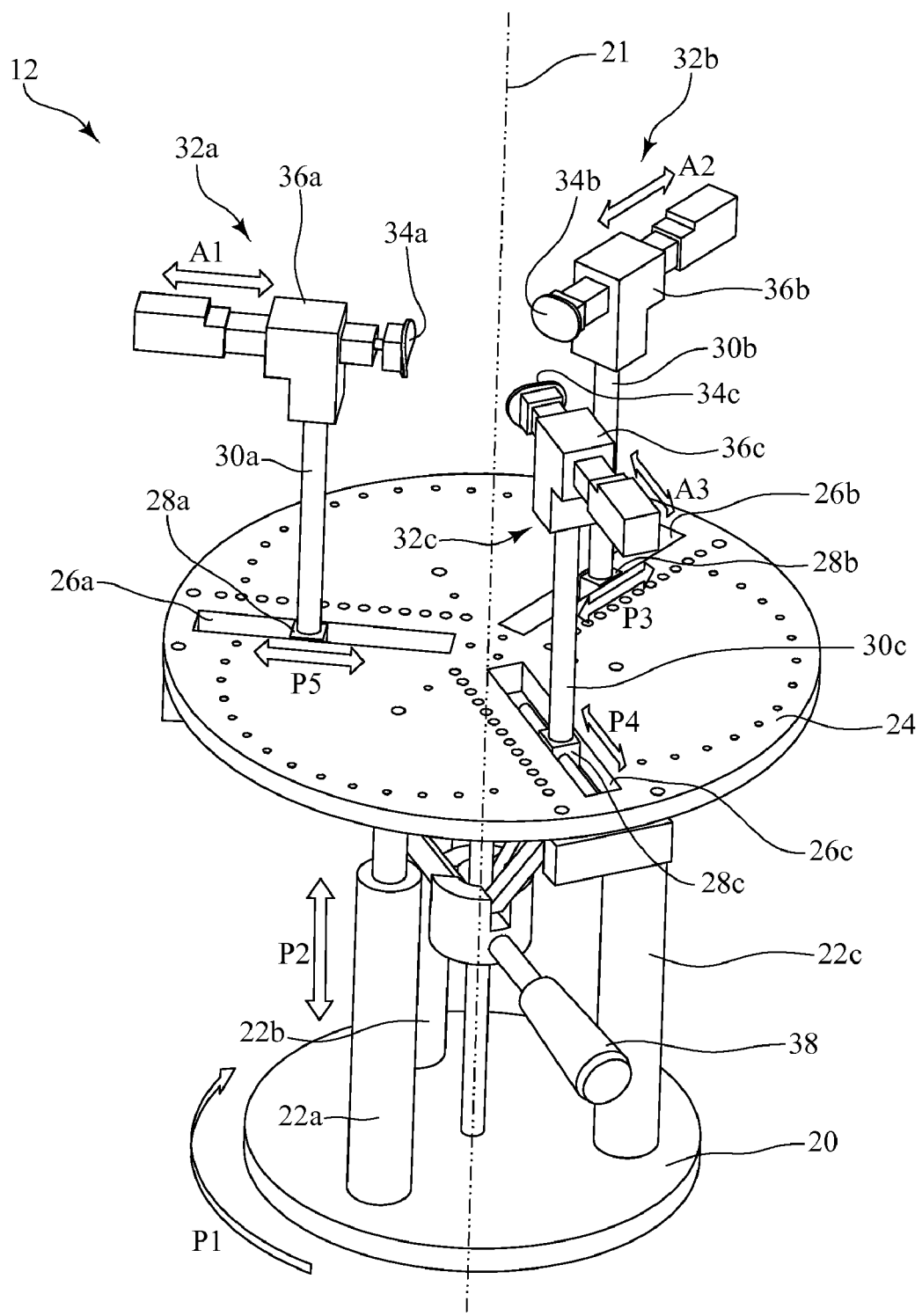
FIG. 4 is an isolated perspective view of a manipulation system of the system of FIG. 3.

FIG. 4 best shows the components of the exemplary manipulation system 12, including a rotary base 20 defining a central axis 21, a plurality of telescoping columns 22a, 22b, 22c extending upward from the rotary base 20, an actuator base 24 supported on the plurality of telescoping columns, the actuator base 24 having a plurality of radial slots 26a, 26b, 26c equally spaced around the central axis 21, sliders 28a, 28b, 28c respectively positioned in each slot 26a, 26b, 26c, support links 30a, 30b, 30c respectively extending upward from each slider 28a, 28b, 28c, and force applicators 32a, 32b, 32c respectively supported on each support link 30a, 30b, 30c.

The rotary base 20 is rotatable about the central axis 21 and lockable in place.

The plurality of telescoping arms 22a, 22b, 22c are extendable in a vertical direction and lockable in place.

The sliders 28a, 28b, 28c are preferably linked for coordinated radial movement along the slots 26a, 26b, 26c with respect to the central axis 21. The sliders 28a, 28b, 28c are also lockable in place.

Each of the force applicators 32a, 32b, 32c has a respective end effector (i.e. contoured link) 34a, 34b, 34c positioned for engaging a surface of the breast and a end effector actuator (i.e. drive mechanism) 36a, 36b, 36c for effecting linear movement to the respective end effector 34a, 34b, 34c. Further, each of the force applicators 32a, 32b, 32c includes an integral end effector (contoured link) position sensor for measuring or sensing the position of the respective end effector 34a, 34b, 34c.

A handle assembly 38 connects to the sliders 28a, 28b, 28c.

The exemplary manipulation system 12 shown in FIG. 4 has three degrees of actuation (DOA) and five passive degrees of freedom (DOF). Block arrows P1 through P5 represent DOF, and block arrows A1 through A3 represent the DOA. The force applicators 32a, 32b, 32c are positioned 120° apart.

In the exemplary manipulation system 12, the force applicators 32a, 32b, 32c weigh 37 g, have dimensions of 94 mm×18 mm×18 mm, have a stroke of 50 mm and have a force capability of 45 N with maximum speed of 2.5 mm per second. The end effector position sensors are on-board servo controllers for precise positioning of the end effectors 34a, 34b, 34c. The end effectors 34a, 34b, 34c are contoured for maximum contact with the surface of the breast. Each end effector 34a, 34b, 34c is made of semi-hard plastic to avoid rupturing the skin. The force applicators 32a, 32b, 32c are mounted on the support links 30a, 30b, 30c which are driven using the sliders 28a, 28b, 28c for coordinated movement of the force applicators 32a, 32b, 32c along the radial direction (P3, P4, P5). The slots 26a, 26b, 26c of the actuator base 24 are 120° apart for accommodating radial movement of the support links 30a, 30b, 30c. The actuator base 24 can be moved in the vertical direction (P2) using the telescoping columns 22a, 22b, 22c. The exemplary manipulation system 12 is placed on the rotary base 20 that can be rotated (P1) about the central axis 21 and locked in place.

The exemplary manipulation system 12 can be setup in two easy steps: (1) by locking the sliders 28a, 28b, 28c in place using locating pins (not shown) and moving the handle assembly 38 up/down, the actuator base 24 can be positioned such that the force applicators 32a, 32b, 32c are in the plane of the target; and (2) by locking the telescoping columns 22a, 22b, 22c and moving the handle assembly 38 up/down the sliders 28a, 28b, 28c can be moved radially in a coordinated manner until the contoured links 34a, 34b, 34c make contact with the surface of the breast. The manipulation system 12 can also be optionally rotated for convenient access based on the desired location of the instrument insertion site.

The position of the force applicators 32a, 32b, 32c is adjusted to accommodate different breast sizes. Setup time for the manipulation system 12 is minimal since only one control knob needs to be adjusted for positioning the force applicators 32a, 32b, 32c. The open structure of the manipulation system 12 facilitates easy positioning and access for the instrument guidance device 16 and image acquisition system 14 (see FIG. 3).

Figure 5:
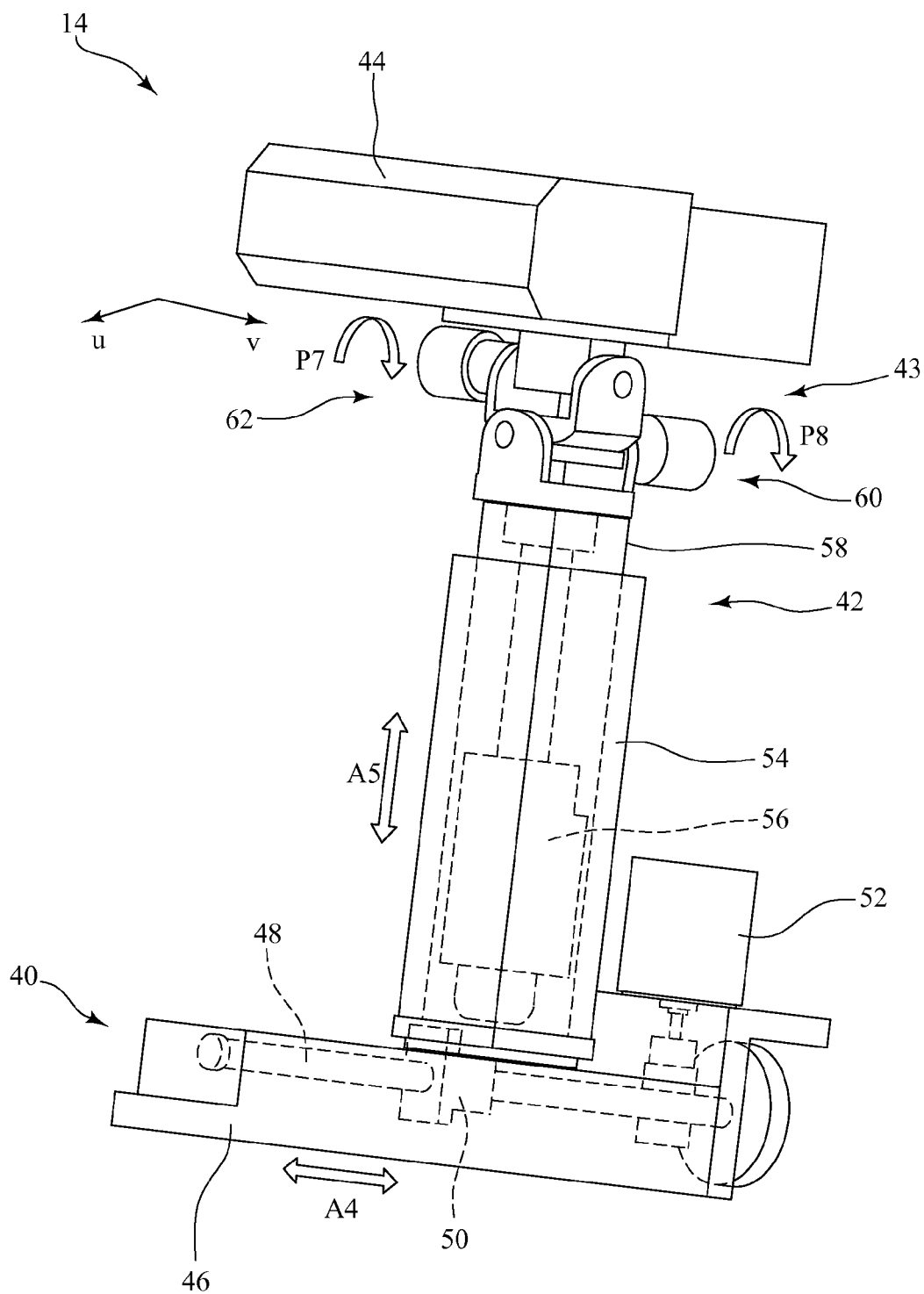
FIG. 5 is an isolated perspective view of an image acquisition system of the system of FIG. 3.

FIG. 5 best shows the components of the exemplary image acquisition system 14, including an imaging probe horizontal drive mechanism 40, an imaging probe vertical drive mechanism 42, an image acquisition system two-axis coupling 43, and an imaging probe 44. The imaging probe horizontal drive mechanism 40 and the imaging probe vertical drive mechanism 42 make up an exemplary image acquisition system drive mechanism for moving the imaging probe 44 in at least two dimensions with respect to the breast. The imaging probe 44, such as an ultrasound (US) probe, obtains data for generating a two-dimensional image corresponding to an image plane within the breast. As described below, in use the imaging probe horizontal drive mechanism 40 and the imaging probe vertical drive mechanism 42 are actuated to move the imaging probe 44 to maintain contact with the breast and to track the location of the target if the target moves out of the imaging plane (i.e. the field of view of the imaging probe).

In the exemplary image acquisition system 14, the horizontal drive mechanism 40 is an elongated slide 46 movably mounted on the actuator base 24 (FIG. 3) in a radial horizontal orientation with respect to the central axis 21 (FIG. 4). The elongated slide 46 has a lead screw 48 longitudinally positioned within the elongated slide 46, a pinion mount 50 engaging the lead screw 48, and a motor 52 for rotating the lead screw 48 to drive the pinion mount 50 horizontally along the length of the lead screw. The motor has an embedded sensor for measuring the horizontal position of the pinion mount 50.

The vertical drive mechanism 42 of the exemplary image acquisition system 14 is a telescoping finger 54 extending upward from the pinion mount 50. The telescoping finger 54 has a telescoping finger linear actuator 56 for effecting vertical movement of an upper end 58 of the telescoping finger 54. The linear actuator 56 also has an embedded sensor for measuring the vertical position of the upper end 58 of the telescoping finger 54.

The image acquisition system two-axis coupling 43 is supported by the upper end 58 of the telescoping finger 54. The two-axis coupling 43 has a first pivot joint 60 for allowing rotation about a first horizontal radial axis (the u-axis, as shown) and a second pivot joint 62 for allowing rotation about a second horizontal axis orthogonal to the first horizontal radial axis (the v-axis, as shown). Embedded sensors measure the position of the first pivot joint 60 and the second pivot joint 62. The two-axis coupling 43 supports the imaging probe 44.

The exemplary image acquisition system 14 has two DOA (A4, A5) and three DOF (P6, P7, P8). The two-axis coupling 43 has two DOF (P7 and P8). The imaging plane of the imaging probe 44 is the u-v plane. The two-axis coupling 43 can rotate about the u-axis (roll, P7) and the v-axis (pitch, P8) for orienting the imaging probe 44 such that the imaging plane is parallel to the surgical instrument insertion path. Vertical motion (A5) is achieved using the telescoping finger linear actuator 56 mounted inside the telescoping finger 42. The telescoping finger 42 is mounted on the elongated slide 46 that is moved using the lead screw 48 driven by the motor 52 for horizontal motion (A4). The exemplary image acquisition system 14 moves the imaging probe 44 along A4 to make and maintain contact with the breast, and also slides the imaging probe 44 along A5 for tracking the location of the target if the target moves out of the imaging plane (u-v). Collectively, the image acquisition system sensors make up an imaging probe position sensor for sensing a position of the imaging probe 44.

Figure 6:
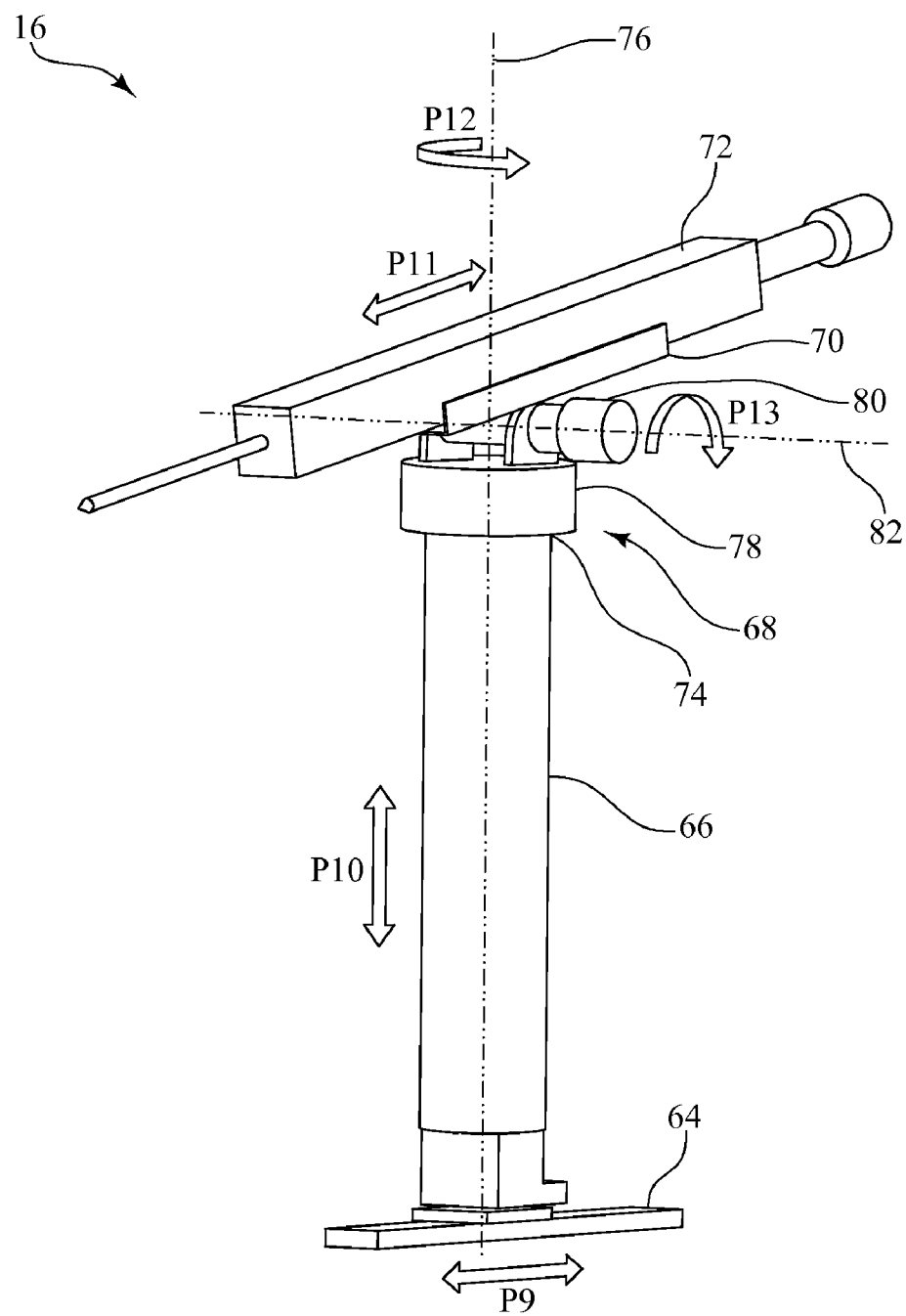
FIG. 6 is an isolated perspective view of surgical instrument guidance device of the system of FIG. 3.

FIG. 6 best shows the components of the instrument guidance device 16, including a guide rail 64, an instrument guidance device telescoping finger 66, an instrument guidance device two-axis coupling 68, an instrument slide 70, and an instrument 72.

The guide rail 64 is movably mounted on the actuator base 24 (FIG. 3) in a radial horizontal orientation with respect to the central axis 21 (FIG. 4).

The telescoping finger 66 is mounted on and slidable along the guide rail 64. The telescoping finger 66 extends upward from the guide rail 64, and has an upper end 74 that is extendable in a vertical direction. The telescoping finger 66 defines a telescoping finger vertical axis that is parallel to the central axis. Embedded sensors provide horizontal and vertical positional information of the telescoping finger upper end 74.

The two-axis coupling 68 is supported on the telescoping finger upper end 74, and includes a third pivot joint 78 for allowing rotation about the telescoping finger vertical axis 76, and a fourth pivot joint 80 for allowing rotation about a horizontal axis 80. Embedded sensors provide positional information of the two-axis coupling 68 with respect to the telescoping finger vertical axis 76 and the horizontal axis 80.

The instrument slide 70 is supported by the two-axis coupling 68 and slidably receives the instrument 72. Another embedded sensor provides positional information for the instrument 72 with respect to the instrument slide 70.

The instrument guidance device embedded sensors, collectively, make up an instrument path sensor for sensing a characteristic of the path of the instrument 72.

The instrument guidance device 16 is a five DOF (P9-P13) platform which facilitates positioning and orienting of the surgical instrument insertion direction based on feedback from the imaging probe 44 of the target location and other critical anatomical structures. The instrument guidance device 16 is sufficient for positioning and orienting any object in 3D Euclidean space. Thus, the surgical instrument 72 is capable of reaching any target in the breast.

The guide rail 64 allows adjustment of the distance (P9) of the instrument guidance device 16 (P9) from the breast. The telescoping finger 66 facilitates height adjustment (P10). The two-axis coupling 68 provide yaw and pitch motion (P12 and P13) for orientation. The surgical instrument slide 70 is used for insertion of the surgical instrument into the breast along the insertion path direction (P11).

Returning now to FIG. 3, the manipulation system 12, image acquisition system 14 and instrument guidance device 16 are integrated in such a manner that the exemplary system is compact and easy to setup and operate. The image acquisition system 14 and the instrument guidance device 16 are mounted on the actuator base 24 of the manipulation system 12. Both the image acquisition system 14 and the instrument guidance device 16 can passively rotate (P14 and P15) about the central axis 21 and, thus, can be placed at any angle (the current configuration shows steps of 10 degrees) between two adjacent force applicators 32a, 32b, 32c (FIG. 4) of the manipulation system 12. The center of the actuator base 24 is chosen to be the global reference frame. A kinematic relationship determines the global position of both the image plane (u-v plane in FIG. 5) and the surgical instrument insertion path direction (P11) (FIG. 6).

The exemplary system has five actuators, as follows: three actuators (A1, A2, A3) for the manipulation system 12 and two actuators (A4, A5) for the image acquisition system 14. The exemplary system also has 10 potentiometers for measuring joint angles of the various links: three potentiometers measure the extension of the manipulation system linear actuators 32 (A1, A2, A3), five potentiometers measure joint positions of the image acquisition system 14 (A4, A5, P6, P7, P8), and two potentiometers measure joint positions of the surgical instrument guidance device (P12-P13). In one embodiment, a 16 channel, 16-bit analog input board (PCI-DAS6034, Measurement Computing) is used for reading the potentiometer data for input to a control algorithm, and an eight channel, 16-bit analog output board (PCI-DDA08/16, Measurement Computing) is used for controlling the actuators (A1-A5). The exemplary system is preferably mounted on a mobile platform for ease of transportation.

Advantageously, the exemplary system aids the clinician in biopsy and other surgical procedures. The first step is identifying the target through the image from the imaging probe 44. The clinician operates the imaging probe 44 to identify the target on an imaging screen. Once the target is identified and located, the image acquisition system 14 tracks the target. Next, the insertion path of the surgical instrument is manually set by the clinician using the instrument guidance device 16. Once the surgical instrument guidance device is set, the insertion path is automatically determined from the sensor readings. The manipulation system 12 is automatically updated with the target location information as obtained from the image and the insertion path information. Now as the clinician begins to insert the surgical instrument, if the target deflects away from the needle path the manipulation system generates appropriate controlled force to move the target back to the insertion path (by computing the distance between the target and the surgical instrument path, as discussed below).

II. CONTROL FRAMEWORK

Figure 8:
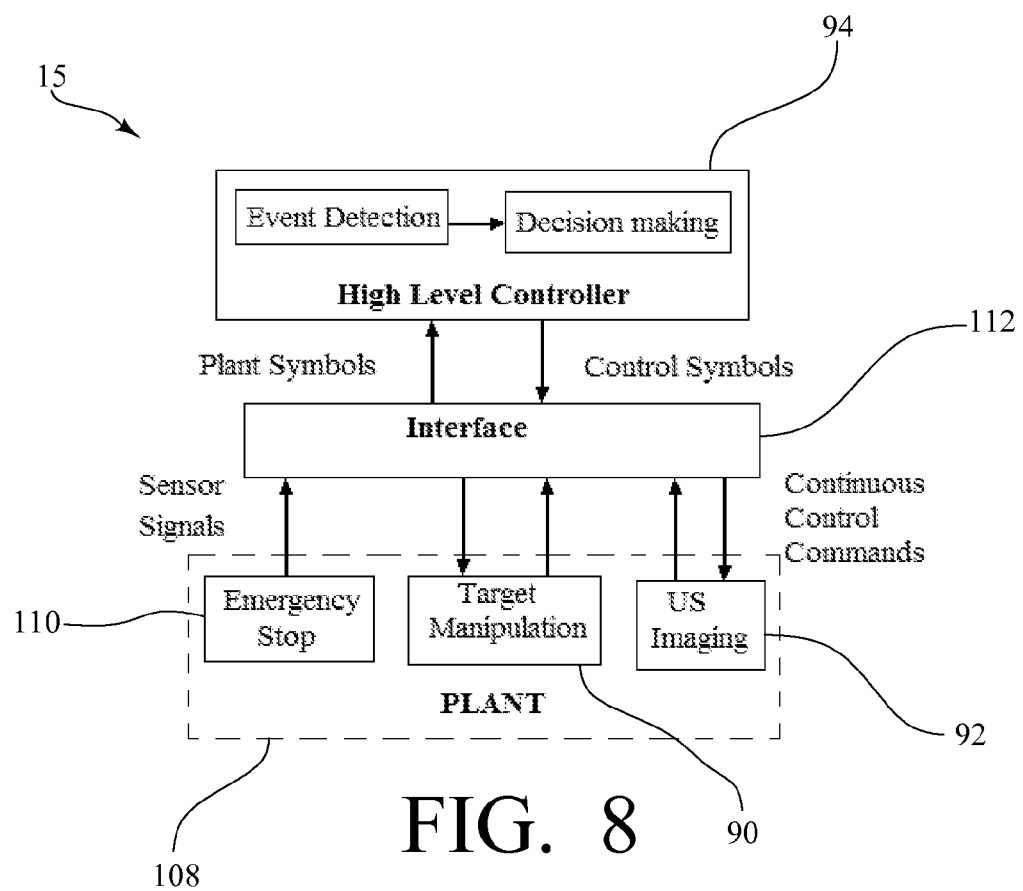
FIG. 8 is a block diagram of an exemplary control means for controlling the system of FIG. 2.

FIG. 8 shows a control framework of an exemplary control means for the system, including a target manipulation system controller 90, an image acquisition system controller 92 (i.e. a detection means), and a high level supervisory controller 94. The high level supervisory controller 94 coordinates the target manipulation system controller 90 and the image acquisition system controller 92 for smooth operation. This framework is described below.

A. Low Level Controller for Target Manipulation

FIG. 1A-FIG. 1C illustrate a process of inserting a needle 96 into a breast 98. To remove a tissue sample, the physician inserts the needle 96 through an incision in the breast 98. The two dimensional plane of the figure represents a horizontal plane passing through a target 100 (e.g. a tumor). In the figures, a simplified anatomy for the breast 98 is shown. In reality, breast tissue is inhomogeneous and its biomechanical properties are nonlinear. Hence, if the tip of the needle 96 reaches an interface between two different types of tissue, its further insertion will push the tissue, instead of piercing it, causing unwanted deformations. These deformations move the target 100 away from its original location, as shown in FIG. 1B. Actuators 32a, 32b, 32c are positioned around the breast 98, as shown in FIG. 1C, that apply forces on the surface of the breast 98 based on an image of the target 100 obtained from an imaging probe 44 to guide the target 100 towards the line of insertion of the needle 96.

During the biopsy procedure, the needle 96 is inserted into the breast 98 at a shallow angle (away from the chest wall) to the horizontal plane containing the target 100. The desired target position is the point where the line of insertion (of the needle 96) intersects the plane containing the target 100. While one can choose any plane that contains the target 100 and has an intersection with the line of needle insertion, the horizontal plane is chosen for simplicity. The desired target position is determined by a planner based on the actual target 100 location and needle 96 direction. The target manipulation system controller 90 (FIG. 8) acts on the position error to guide the target 100 towards the desired location. The target 100 position only needs to be controlled in two dimensions (horizontal plane) to be able to successfully position the target 100 along the line of insertion of the needle 96. To control the target 100 position in two dimensions, three actuators 32a, 32b, 32c are distributed around the breast 98 which apply normal compressive forces on the surface. In this framework, the force exerted by the needle 96 is considered a disturbance to the system. The target manipulation system controller 90 (FIG. 8) is designed such that the effect of the needle 96 force (disturbance) on the breast 98 is minimized.

Through extensive simulations and experimental testing it has been determined that PI (proportional-integral) and PID (proportional-integral including derivative feedback) controllers are suited for the application. The PI control law does not require knowledge of any geometric or mechanical properties of the breast. Filtered target position data is differentiated to provide derivative control action.

Figure 7:
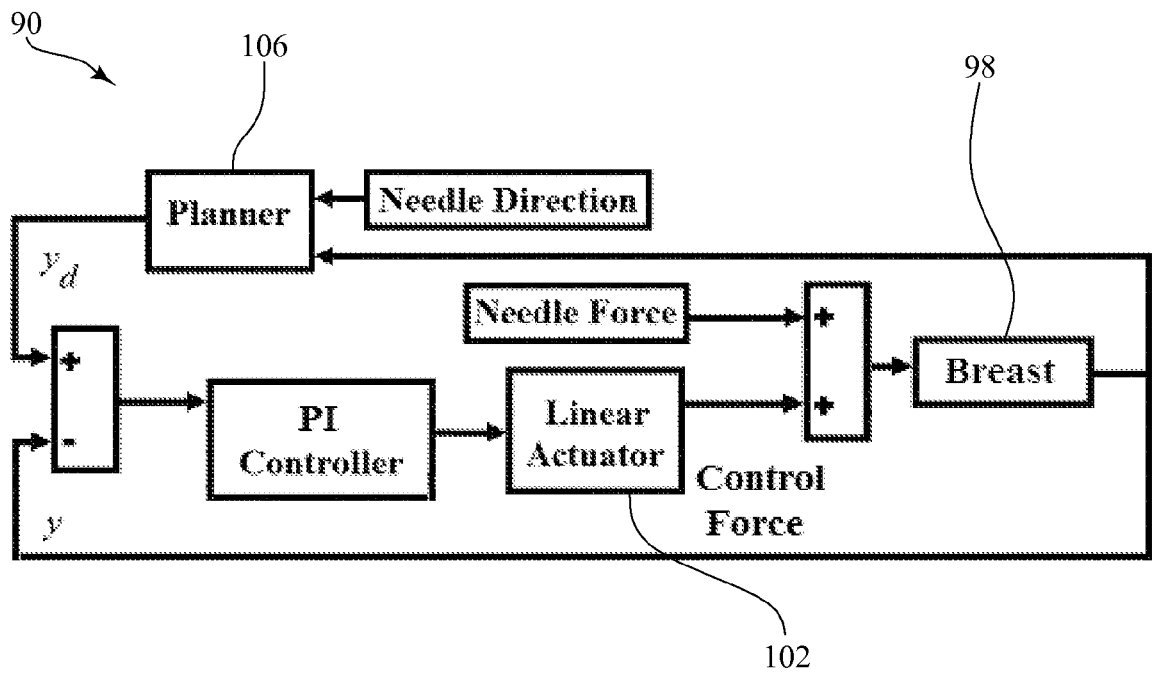
FIG. 7 is a block diagram of a low level control structure for controlling the manipulation system of FIG. 4.

FIG. 7 is a schematic of the target manipulation system controller 90. Target position data within the breast 98 is obtained through feedback from the imaging probe 44 (FIG. 1C). The desired target 100 position ($y_d$) is determined by a planner 106 based on the current target location (y) and needle 96 direction. The desired target 100 position is always along the line of insertion of the needle 96. The target manipulation system controller 90 acts on the position error and drives the actuators 102 to position the target 100 at the desired location. The force exerted by the needle 96 is the disturbance to the system. The effect of controller wind-up when tissue compression is high can be mitigated through saturation feedback compensation (see: Mallapragada et al., 2007 [21]).

The target manipulation system controller 90 may include derivative feedback (PID control) in which target position data is differentiate filtered to provide derivative control action. This reduces settling time for the target 100 position.

B. Low Level Controller for US Imaging

Returning to FIG. 1C, tracking the location of a target 100 (3D coordinates) using a 2D imaging probe 44 (such as a US imaging probe) requires knowledge of the position of the imaging probe 44 and coordinates of the target 100 in the image plane of the probe. Potentiometers are used to measure the position of the probe 44. Coordinates of the target 100 are extracted using an image processing algorithm, if the target 100 is in the imaging plane. If the target 100 is out of the imaging plane, there is uncertainty in determining the location of the target 100 with respect to the imaging plane i.e., there is no information regarding the location of the target 100 in a direction perpendicular to the imaging plane. A search strategy exhaustively searches for the target 100 by first determining the direction of maximum likelihood for locating the target 100 based on (1) direction of needle 96 insertion and (2) direction of force application by the actuators 32a, 32b, 32c. The direction of maximum likelihood is a function of both the above factors since the net force on the target 100 (and the breast) is determined by the sum of the forces applied by the needle 96 and the external actuators 32a, 32b, 32c. Since the US probe 44 is just in contact and does not apply any significant amount of force on the breast 98, it does not affect the movement of the target 100.

The direction of maximum likelihood determined above provides an intelligent starting point to search for the target 100. It is not possible to accurately predict the direction of target movement due to complex nature of interaction dynamics and tissue inhomogeneity within the breast 98. Once the direction of maximum likelihood is determined, the imaging probe vertical drive mechanism 42 (FIG. 5) (a position controlled linear actuator) moves the Imaging probe 44 along this direction for a specified distance. If during this time, the target 100 is located, the imaging probe vertical drive mechanism 42 stops moving to keep the target in the image plane. If the target 100 is not located by moving along this direction, then the imaging probe vertical drive mechanism 42 reverses and moves along the opposite direction to locate the target 100. Since typically the target movement is not greater than 10 mm, by moving the US imaging 44 probe 7. 5 mm in each direction (total 15 mm) the target should be locatable.

It should be noted that other search algorithms, such as a brute force search algorithm, may be utilized to locate the target 100. As such, other search algorithms would be considered to be within the scope of the invention as claimed.

Due to high acoustic impedance of air, the imaging probe 44 has to be in contact with the breast 98 for imaging the target 100. Surface deformation due to target manipulation and needle insertion may result in the imaging probe 44 losing contact with the breast 98. Loss of contact has to be detected and the imaging probe 44 has to be moved to reestablish contact with the breast 98. The region in the image close to the edge (where the Imaging probe 44 makes contact with the surface) is used to detect the contact state of the Imaging probe 44. This region is extracted from the US image and Otsu's method is used to estimate the grayscale threshold for the region. When the imaging probe 44 is in contact with the surface the threshold is small, and when the imaging probe 44 breaks contact with the surface the threshold increases. This change in the threshold is used to infer the contact state of the imaging probe 44.

B. High Level Supervisory Controller

Returning to FIG. 8, the fundamental theoretical framework that is used to integrate the target manipulation system controller 90 and the image acquisition system controller 92 is based on hybrid system theory (see: Antsaklis et al., 2003 [22]). In particular, a high level supervisory controller 94 monitors and coordinates the target manipulation system controller 90 and the image acquisition system controller 92 based on discrete events. The high level supervisory controller 94 activates the target manipulation system controller 90 and the image acquisition system controller 92 at any given time based on certain events that take place during the biopsy procedure.

The high level supervisory controller 94 includes a discrete decision process that is typically a discrete-event system (DES) described by a finite state automaton. The proposed high level supervisory controller 94 makes decisions about the task that is required for robotic assistance during biopsy. The high level supervisory controller 94 and a plant 108 (an emergency stop 110, as well as the target manipulation system controller 90 and the image acquisition system controller 92) cannot communicate directly in a hybrid control system because each utilizes different types of signals. Thus an interface 112 is required which can convert continuous-time signals to sequences of symbols and vice versa. In order for the high level supervisory controller 94 to decide the necessary control actions, the state information from the plant 108 is observed by a process monitoring module through the interface 112. The interface 112 triggers events pertinent to the task and communicates to a process monitoring block of the high level supervisory controller 94. Once these events are triggered, a decision making module of the high level supervisory controller 94 determines what actions need to be taken in response to these events. The high level supervisory controller 94 instructions are sent to the target manipulation system controller 90 and the image acquisition system controller 92 through the interface 112, which then execute the actions. This architecture is flexible and extendable in the sense that new events can be included and detected by simply monitoring the additional state information, and accommodated by introducing new low level controllers.

The high level supervisory controller 94 is a discrete-event system (DES) deterministic finite automaton, which is specified by:

$$D = (\tilde{P}, \tilde{X}, \tilde{R}, \psi, \lambda)[22]. \qquad (1)$$

Here $\tilde{P}$ is the set of discrete states. Each event is represented as a plant symbol, where $\tilde{X}$ is the set of such symbols, for each discrete state. The next discrete state is activated based on the current discrete state and the associated plant symbol using the following transition function: $\psi: \tilde{P} \times \tilde{X} \to \tilde{P}$. In order to notify the low level controller the next course of action in the new discrete state, the controller generates a set of symbols, called control symbols denoted by $\tilde{R}$ using an output function: $\lambda: \tilde{P} \to \tilde{R}$. The action of the high level control is described by the following equations:

$$\tilde{p}_j[n] = \psi(\tilde{p}_i[n-1], \tilde{x}_k[n]), \qquad (2)$$

$$\tilde{r}_c[n] = \lambda(\tilde{p}_j[n]), \qquad (3)$$

where $\tilde{p}_i, \tilde{p}_j \in \tilde{P}$, $\tilde{x}_k \in \tilde{X}$, $\tilde{r}_c \in \tilde{R}$ represent the index of discrete states. k and c represent the index of plant symbols and control symbols respectively. n is the time index that specifies the order of the symbols in the sequence.

The high level supervisory controller 94 first detects state information from the plant 108 through the interface 112, and then determines the actions to be taken in response to this information. The state information from the plant 108 can be a continuous signal or a discrete value. Let $S_{Mn}$, $S_{In}$ and $S_{En}$ represent the sets of robot and manipulation, imaging and emergency state information respectively. The signal detected from the manipulation system 12 is: a) Actuator overload ($S_{M1}$, 0—actuators not overloaded; 1—actuators overloaded). Three signals from the US imaging state information are detected: a) contact condition of the US probe ($S_{I1}$, 0—contact; 1—no contact); b) presence of target in the image plane ($S_{I2}$, 0—target in image plane; 1—target not in image plane); and c) US probe position ($S_{I3}$). An emergency signal is also monitored to detect when the stop button is pressed ($S_{E1}$, 0—no emergency; 1—emergency stop). Position of the imaging probe 44 is the only continuous signal, all other signals are discrete values. In this procedure, the following plant states are defined: $\tilde{P}$: manipulation, contact initiation, target tracking and stop. Manipulation ($\tilde{p}_1$) implies that target manipulation is activated. Contact initiation ($\tilde{p}_2$) means that the US probe is moved to make contact with the surface of the breast. Target tracking ($\tilde{p}_3$) means that the search algorithm is activated to locate the target. Stop ($\tilde{p}_4$) means that the entire system is disabled.

State information from the plant is monitored to trigger relevant events to modify the task. When these events are triggered, the interface 112 provides the necessary plant symbol ($\tilde{x}$) to the high level supervisory controller 94. Six events are defined for the high level supervisory controller 94. However, the number of events can be easily extended. Events are reset at the beginning of task execution. Additionally, the triggered event is reset when a new event occurs.

The symbol "Limits" is used to represent the motion limits of the range of movement of the imaging probe 44. When the target manipulation force applicators 32a, 32b, 32c are not overloaded, the imaging probe position is within limits and the emergency stop is not detected, event $E_1$ is triggered. When any one of the above conditions is not satisfied, event $E_2$ is triggered. When the US probe breaks/makes contact with the surface, events $E_3/E_6$ are triggered. When the target moves out of/into the imaging plane, events $E_4/E_5$ are triggered. Plant symbols are designed based on the events shown in Table 1.

TABLE 1

| Signal | Event triggered | Plant Symbol |
|---|---|---|
| $(S_{M1} = 0) \land (S_{I3} < \text{Limits}) \land (S_{E1} = 0)$ | $E_1 = 1$ | $\tilde{x}_1$ |
| $(S_{M1} = 1) \lor (S_{I3} > \text{Limits}) \lor (S_{E1} = 1)$ | $E_2 = 1$ | $\tilde{x}_2$ |
| $S_{I1} = 1$ | $E_3 = 1$ | $\tilde{x}_3$ |
| $S_{I2} = 1$ | $E_4 = 1$ | $\tilde{x}_4$ |
| $S_{I1} = 0$ | $E_5 = 1$ | $\tilde{x}_5$ |
| $S_{I2} = 0$ | $E_6 = 1$ | $\tilde{x}_6$ |

Figure 9:
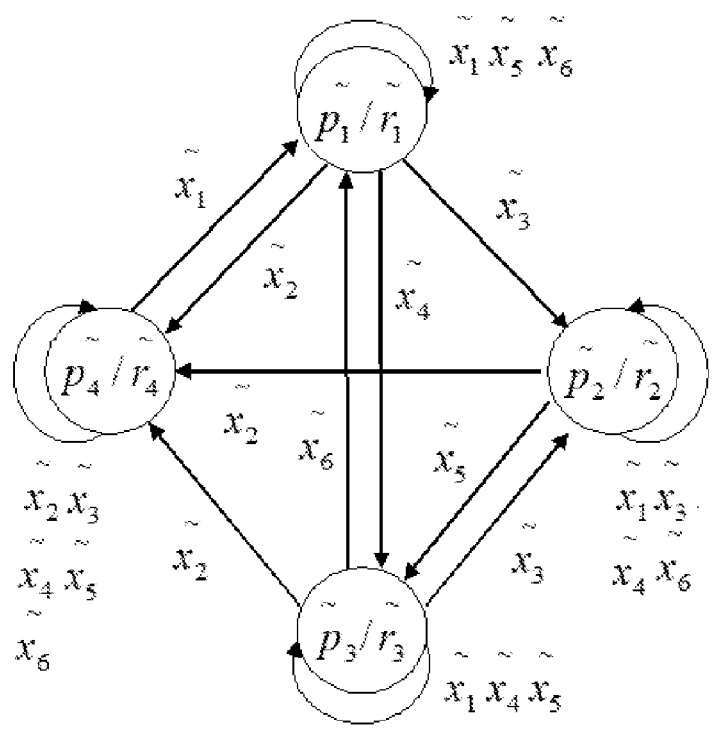
FIG. 9 is a state diagram of an exemplary control of the high level supervisory controller of FIG. 8.

When an event is triggered, the corresponding plant symbol ($\tilde{x}$) is generated by the interface 112. The current state ($\tilde{p}$) and the plant symbol ($\tilde{x}$) are used by the high level supervisory controller 94 to determine the next state. The control mechanism of the proposed high level supervisory controller 94 is shown in FIG. 9. The high level supervisory controller 94 generates a control symbol for each state according to the following output function:

$$\lambda(\tilde{p}_i) = \tilde{r}_i \text{ for } i=1, 2, 3, 4 \qquad (4)$$

Only one state is active at a time and, therefore, a control symbol is uniquely assigned for each state. Any event that generates a plant symbols along with the current state information determines the next state and as a result the corresponding control symbol. Since the low-level assistive controller cannot interpret the control symbols, the interface 112 converts them into enable/disable signals based on the control policy. The control symbols and their corresponding control policies are given in Table 2.

TABLE 2

| Output symbol | Control Policy |
|---|---|
| $\tilde{r}_1$ | Enable target manipulation |
| $\tilde{r}_2$ | Enable contact initiation |
| $\tilde{r}_3$ | Enable target tracking |
| $\tilde{r}_4$ | Disable all systems |

The presently-disclosed subject matter is further illustrated by the following specific but non-limiting examples. The following examples may include compilations of information that are representative of information gathered at various times during the course of development and experimentation related to the presently-disclosed subject matter.

III. EXPERIMENTAL RESULTS

A. Phantom Preparation

A deformable plastic phantom with a stiff inclusion (a plastic insert placed in the phantom to simulate a tumor) is created to test the efficacy of the controller in positioning the inclusion at a desired location. The phantom is a cylindrical structure (radius 60 mm, height 35 mm) made of deformable thermoplastic. The inclusion is a plastic sphere (diameter 14 mm) that is much stiffer than the phantom. The inclusion is the target in the following experiments. The material used to make the phantom consists of two parts: super soft thermoplastic (Plastisol) and softener. The ratio of the two parts determines the elastic properties of the phantom. Increasing the amount of softener decreases the stiffness of the phantom.

Figure 10:
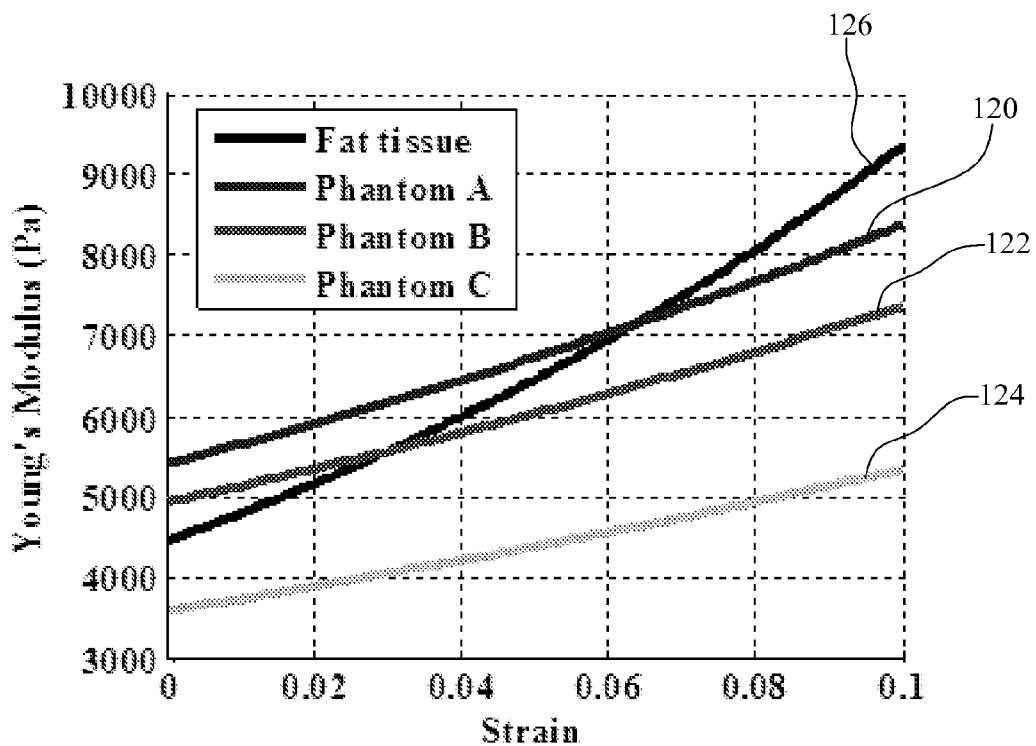
FIG. 10 is a graph of the Young's moduli of several experimental deformable plastic phantom used for experimental purposes.

FIG. 10 shows three different phantoms (Phantom A 120, Phantom B 122, and Phantom C 124) that are constructed with different ratios of plastic and softener. Uniaxial compression tests are performed on the phantoms to determine their elastic properties. Nominal stress—strain values are computed from force—displacement data measured during the compression test. Elastic moduli of the phantoms are determined by an exponential fit of the stress—strain curve, Wellman, 1999 [24]. Using the notation in [24] the stress—strain relationship is given by $$\sigma_n^* = \frac{b^*}{m^*}(e^{m^* \epsilon_n} - 1), \qquad (5)$$

where $\sigma_n^*$ is the nominal stress and $\epsilon_n$ is the nominal strain. $b^*$ and $m^*$ are the exponential fit parameters. The Young's modulus is given by $$E = b^* e^{m^* \epsilon_n}. \qquad (6)$$

FIG. 10 shows a plot of the Young's moduli of the phantoms 120, 122, 124. Breast fat tissue data 126 shown in FIG. 10 is presented by Wellman, 1999 [24]. The phantoms have Young's moduli similar to that of fat tissue in the breast.

B. Experimental Setup

The ability to control the position of a target inside the breast, and to dynamically track the location of a target in real-time using a 2D US probe have been investigated using phantoms. An experimental testbed is constructed to test the efficacy of the proposed technique in positioning the target at a desired location by applying force on the surface of the phantom.

Position feedback of the target is obtained using a 2D US imaging system Toshiba ECCO-CEE (model SSA-340A). Image frames from the US system are sent to a computer (1.6 GHz and 2 GB RAM) running image processing algorithm in Matlab. Image frames are processed to extract position data of the inclusion. The target position data is communicated serially to a microcontroller (Freescale 68HC912B32, 8 MHz clock frequency). The microcontroller outputs this data in a 16 bit parallel format. This data is read by another computer (1.6 GHz and 1 GB RAM) using a data acquisition card (Measurement computing PCIM DDA06/16). This computer runs the control algorithm and outputs control signals to power amplifiers for driving the linear actuators. The linear actuators are lead screw driven with inbuilt potentiometers. They have a no load speed of 50 mm/s and a load capacity of 88N at 25% duty cycle.

C. Experiments

Experiment 1

To Demonstrate Accuracy of Target Positioning Using External Force on the Surface of the Phantom During Needle Insertion For the first experiment, the target is initially located at the origin and the needle is inserted along the Y axis. Due to inhomogeneity in the phantom the target moves away from the needle path during insertion. Linear actuators are positioned along the X axis to steer the target towards the needle path (Y axis). During this experiment the force applied by the needle on the phantom is treated as a disturbance to the system. The task of the controller is to position the target on the Y axis. The position of the target along the Y axis is not controlled since the needle will intersect with the target no matter where it is located on the Y axis. In this experiment a PI controller is used for controlling the position of the target.

Figure 11:
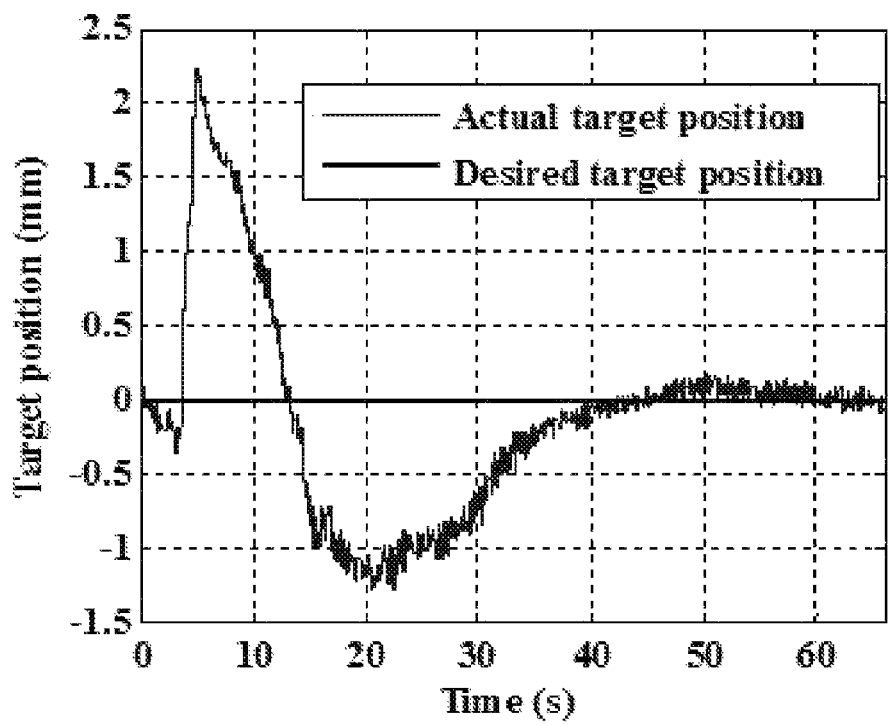
FIG. 11 is a graph of the position response of a target in an inhomogeneous phantom of a first experiment.

FIG. 11 shows a plot of the position response of the target (along the X axis) in an inhomogeneous phantoms. This phantom has two kinds of material with elastic moduli similar to fat and glandular tissue. From FIG. 11, it is observed that the target is initially located on the Y axis (displacement along X axis is zero). As the needle is inserted the target moves away from the Y axis (non zero displacement along X axis). This initiates a control action by the actuators which steer and position the target on the Y axis (displacement along X axis is zero) at steady state. As seen from FIG. 11, the target is steered back to the needle path in about 40 seconds. In all trials, the target was successfully positioned along the needle path.

Figure 12:
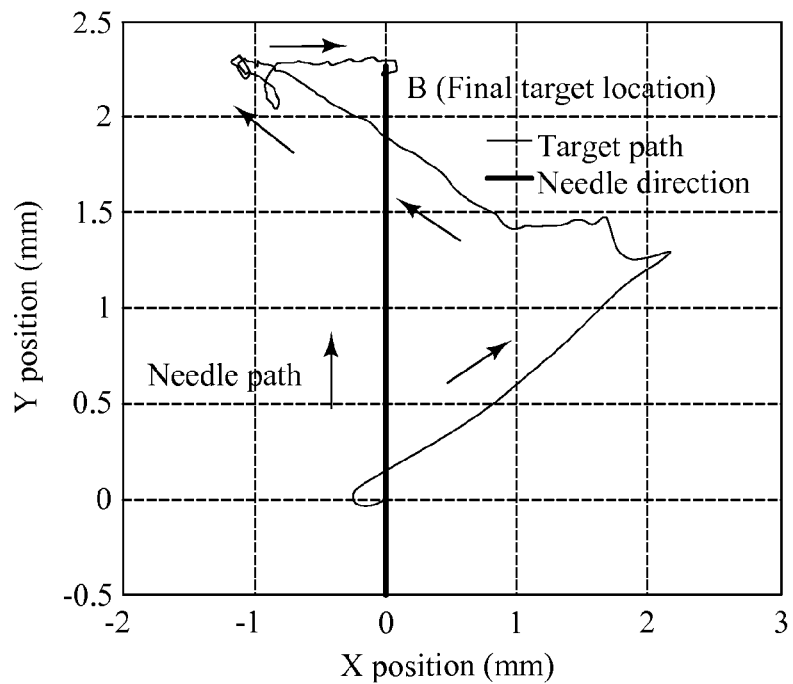

FIG. 12 shows the locus of the target position. As seen from FIG. 12, the target is initially located in the path of the needle (Point A), but as the needle is inserted it deviates away from the path and the PI controlled actuators steer it back towards the line of insertion. The final location of the target is at Point B on the needle path where it meets the needle.

Since the movement of the target along the Y direction is small (~2 mm), the target is in the US image plane during the entire experiment. The US probe did not break contact with the surface of the phantom. Emergency stop is also not activated during the experiment. Hence, the discrete event plant (FIG. 9) stays in the manipulation state ($\tilde{p}_1$) during the course of the experiment.

Experiment 2

To Demonstrate Coordination of Target Positioning and Dynamic Target Tracking During Needle Insertion For the second experiment, linear actuators are used to position the target during a needle insertion task. The target is initially located at the origin and the needle is inserted along the Y axis. The US probe is placed over the phantom such that the imaging plane (XZ plane) is orthogonal to the needle insertion direction. During a biopsy procedure, the imaging plane has to be oriented along the needle insertion direction. In this experiment the US probe is placed orthogonally to demonstrate the ability of the system to track the target when it moves out of the imaging plane during a real-time needle insertion procedure.

In this experiment, during needle insertion, the target moves away from the needle path and out of the imaging plane of the US probe. Two linear actuators positioned along the X axis are used to steer the target towards the needle path (Y axis), similar to Experiment 1. One linear actuator is also used to move the US probe along the Y axis. The task of the controller is to position the target on the Y axis. The position of the target along Y axis is not controlled since the needle will intersect with the target no matter where it is located on the Y axis. In this experiment a PID controller is used for controlling the position of the target.

Figure 13:
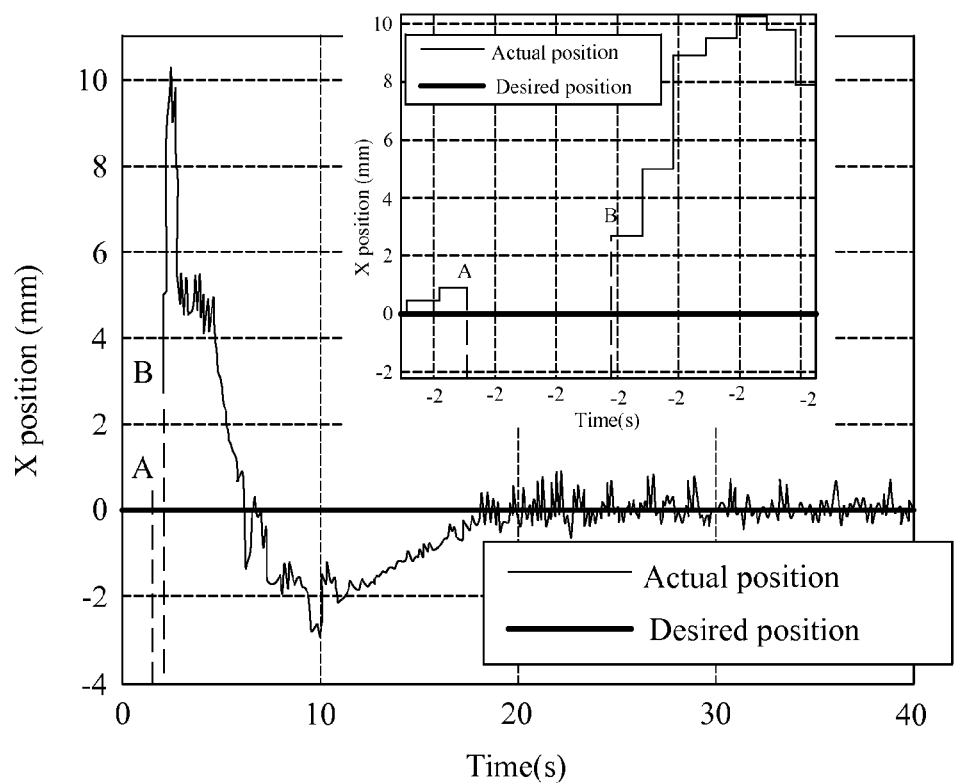
FIG. 13 is a graph of the position response of a target in an inhomogeneous phantom of a second experiment.
Figure 14:
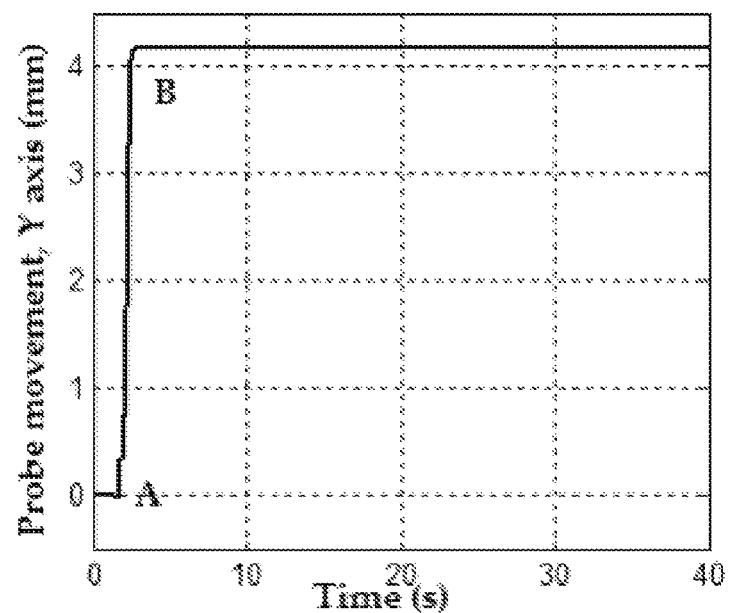
FIG. 14 is a graph of the movement of an ultrasound probe of the second experiment.

FIG. 13 shows a plot of the position response of the target (along the X axis). In FIG. 13, it is observed that the target is initially located on the Y axis (displacement along X axis is zero). As the needle is inserted the target moves away from the Y axis (non zero displacement along X axis). This initiates a control action by the actuators. At point A, the target moves out of the imaging plane of the US probe. This triggers Event $E_4$ (Table 1) and the interface generates plant symbol $\tilde{x}_4$. The high level supervisory controller 94 recognizes this event and generates a control symbol ($\tilde{r}_3$) based on the supervisory control structure (FIG. 9). The interface converts this symbol into a control command that switches the plant state from manipulation ($\tilde{p}_1$) to tracking ($\tilde{p}_3$). In the tracking state, the US probe is moved according to the algorithm outlined above. In this case, the direction of maximum likelihood is along +Y direction because the external actuators do not affect target movement along Y axis and only the needle has a dominating affect on the movement of the target along Y axis. Since the needle is inserted along +Y direction, the target is likely to move in this direction. Hence +Y direction is an intelligent choice for initial movement of the US probe. In this experiment, the target does indeed move along +Y direction and is detected at point B. FIG. 13 (inset) shows a close-up view of the plot between points A and B. Position data is not available between A and B (the dotted lines show a discontinuity in the data and do not represent the position coordinates of the target) for approximately 0.5 seconds. FIG. 14 shows the movement of the US probe along the Y axis between points A and B. At point B event $E_6$ is triggered and the supervisory controller switches the plant state from tracking to manipulation. From point B, the target stays in the imaging plane of the probe and position data is available for the actuators to steer and position the target on the Y axis (displacement along X axis is zero at steady state). As shown in FIG. 13, the target is steered back to the needle path in about 20 seconds. The target could be steered back to the needle path even when the deviation of the target is large (~10 mm).

Two observations from the result of the above experiment are made: 1) the PID controller is more effective than the PI controller for target manipulation (20 seconds (FIG. 13) vs. 40 seconds (FIG. 11)); and 2) target positioning and US imaging can be automated and coordinated in such a manner so as to track the location of the target using the US probe and accurately position the target on the needle path (FIG. 13).

The experimental testbed used in Experiment 1 and Experiment 2 is designed to demonstrate the efficacy of target manipulation and tracking. During the Experiment 1 and Experiment 2, the US probe did not break contact with the surface of the phantom. During a breast biopsy procedure it is possible that the US probe may break contact due to surface deformation. Hence the contact state has to be monitored to maintain contact with the breast.

Experiment 3

To Demonstrate Reliability of the Contact Detection Algorithm

Figure 15A:
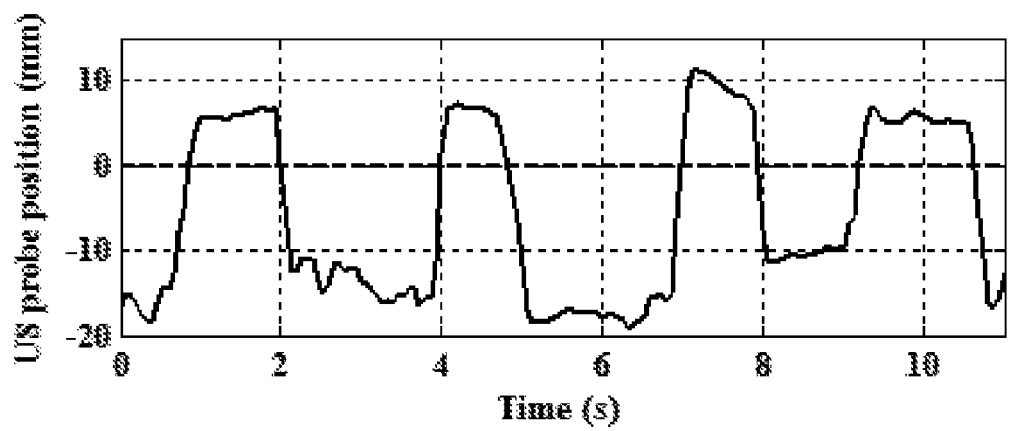
FIG. 15A is a graph of the movement of an ultrasound probe of a third experiment.
Figure 15B:
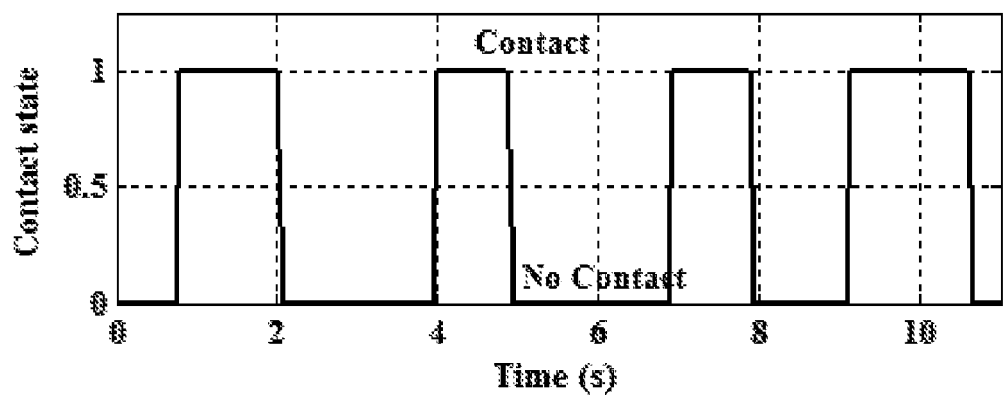
FIG. 15B is a graph of the contact state of the ultrasound probe of the third experiment.

In this experiment target manipulation and tracking are disabled. Position of the phantom is fixed and the US probe is moved normal to the surface of the phantom. FIG. 15A shows the movement of the probe. The X axis represents the surface of the phantom. The US probe is in contact with the phantom if the probe position is nonnegative and the probe breaks contact with the phantom if its position is negative. FIG. 15B shows the contact state of the probe. If the US probe is in contact, it is represented by 1 (True). If the US probe is not in contact, it is represented by 0 (False). The contact state is determined using the algorithm presented above. Comparing FIG. 15A and FIG. 15B, it is observed that the algorithm reliably predicts contact state transitions of the probe. During a biopsy procedure, position data cannot be used to detect contact state transitions due to deformation of the breast. Hence, contact state determined with this technique can be used by the high level supervisory controller 94 (FIG. 8) to facilitate continuous imaging of the target.

The system and method describe herein has several potential advantages, including: (1) success rate of the procedure is increased since the target can be accurately positioned inline with the needle; (2) the entire procedure is fast, making it clinically viable; (3) since the needle is not steered inside the breast, tissue damage is minimized; (4) since multiple insertions are not required, the proposed technique will likely reduce surgeons' fatigue and patient discomfort and preserve structural integrity of the tissue specimen; (5) by improving accuracy of the procedure, it will potentially enhance the diagnostic outcome by reducing false negatives; and (6) geometric and mechanical properties of the breast are not required for precise positioning of the target.

Throughout this document, various references are mentioned. All such references are incorporated herein by reference, including the references set forth in the following list:

[1] American Cancer Society, "Cancer Facts & Figures-2007," http://www.cancer.org/downloads/STT/CAFF2007PWSecured.pdf, accessed on 19 May, 2007.
[2] J. G. Elmore, K. Armstrong, C. D. Lehman, S. W. Fletcher, "Screening for Breast Cancer," Journal of American Medical Association, Vol. 293, No. 10, pp. 1245-1256, March 2005.
[3] O. V. Solberg, F. Lindseth, H. Torp, R. E. Blake, T. A. N. Hernes, "Freehand 3D ultrasound reconstruction algorithms—A review," Ultrasound in Med. and Biol., Vol. 33, No. 7, pp. 991-1009, 2007.
[4] S. P. DiMaio, S. E. Salcudean, "Needle insertion modeling and simulation," IEEE Transactions on Robotics and Automation, Vol. 19, No. 4, October 2003.
[5] D. Stoianovici, L. Whitcomb, J. Anderson, R. Taylor, and L. Kavoussi, "A modular surgical robotic system for image guided percutaneous procedures," in Proc. MICCAI, Vol. 1496, LNCS, pp. 404-410, 1998.
[6] K. Cleary, M. Freedman, M. Clifford, D. Lindisch, S. Onda, and L. Jiang, "Image-guided robotic delivery system for precise placement of theraputic agents," J. Cont. Release, Vol. 74, No. 1, pp 363-368, 2001.
[7] S. Okazawa, R. Ebrahimi, J. Chuang, S. E. Salcudean, R. Rohling, "Hand-held steerable needle device," IEEE/ASME Transactions on Mechatronics, Vol. 10, pp 285-296, June 2005.
[8] S. P. DiMaio, S. E. Salcudean, "Needle steering and model-based trajectory planning," in Proc. MICCAI, Vol. 2878, LNCS, pp. 33-40, 2003.
[9] D. Glozman, M. Shoham, "Image-guided robotic flexible needle steering," IEEE Transactions on Robotics, Vol. 23, No. 3, pp 459-467, June 2007.
[10] M. H. Loser, N. Navab, "A new robotic system for visually controlled percutaneous interventions under CT fluoroscopy", in Proc. MICCAI, Vol. 1935, LNCS, pp. 887-896, 2000.
[11] F. S. Azar, D. N. Metaxas, M. D. Schnall, "Methods for modeling and predicting mechanical deformations of the breast under external perturbations," Medical image Analysis, Vol. 6, pp 1-27, 2002.
[12] R. Alterovitz, K. Goldberg, J. Pouliot, R. Taschereau, I-C. Hsu, "Sensorless planning for medical needle insertion procedures," in Proc. IEEE International Conference on Intelligent Robots and Systems, pp. 3337-3343, October 2003.
[13] V. Mallapragada, N. Sarkar, T. Podder, "Robot assisted real-time tumor manipulation for breast biopsy," IEEE International Conference on Robotics and Automation, May 2008 (accepted).
[14] F. Pierrot, E. Dombre, E. Degoulange, L. Urbain, P. Caron, S. Boudet, J. Gariepy, J. Megnien, "Hippocrate: A safe robot arm for medical applications with force feedback," Medical Image Analysis, Vol. 3, No. 3, pp. 285-300, 1999.
[15] K. Masuda, E. Kimura, N. Tateishi, K. Ishihara, "Three-dimensional motion mechanism of ultrasound probe and its application for tele-echography system," in Proc. IEEE/RSJ International Conference on Intelligent Robots and Systems, pp. 1112-1116, 2001.
[16] A. Vilchis, J. Troccaz, P. Cinquin, K. Masuda, F. Pellisier, "A new robot architecture for tele-echography," in IEEE Transactions on Robotics and Automation, Vol. 19, No. 5, pp. 922-926, 2003.
[17] J. Hong, T. Dohi, M. Hashizume, K. Konishi, N. Hata, "An ultrasound driven needle insertion robot for percutaneous cholecystostomy," Physics in Med. and Biol., Vol. 39, No. 3, 441-455, 2004.
[18] M. A. Vitrani, G. Morel, T. Ortmaier, "Automatic Guidance of a surgical instrument with ultrasound based visual servoing," in Proc. IEEE International Conference on Robotics and Automation, pp. 510-515, 2005.
[19] P. Abolmaesumi, S. E. Salcudean, W. Zhu, M. R. Sirouspour, S. P. DiMaio, "Image-guided control of a robot for medical ultrasound," IEEE Transactions on Robotics and Automation, Vol. 18, No. 1, February 2002.
[20] A. Krupa, G. Fichtinger, G. D. Hager, "Full motion tracking in ultrasound using image speckle information and visual servoing," in Proc. IEEE International Conference on Robotics and Automation, pp. 2458-2464, 2007.
[21] V. Mallapragada, N. Sarkar, T. Podder, "A Robotic System for Real-time Tumor Manipulation During Image Guided Breast Biopsy," in *Proc. IEEE International Conference on Bioinformatics and Bioengineering*, pp. 204-210, October 2007.
[22] P. J. Antsaklis, X. D. Koutsoukos, "Hybrid systems: review and recent progress," In Samad, T., editor. *Software Enabled Control: Information Technology for Dynamical Systems*. NY: Wiley-IEEE; 2003.
[23] P. J. Antsaklis, "A brief introduction to the theory and applications of hybrid systems," in *Proc. IEEE Special Issue on Hybrid Systems: Theory and Applications*, Vol. 88, No. 7, pp. 879-887, 2000.
[24] P. Wellman, "Tactile imaging", PhD dissertation, Division of Engineering and Applied Sciences, Harvard University, MA, 1999.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A system for positioning a target located within soft tissue, comprising:
   an instrument configured to be inserted into the soft tissue along a path;
   a manipulation system including a plurality of force applicators configured to be positioned around the soft tissue containing the target;
   an image acquisition system including an imaging probe for obtaining data for generating an image of the soft tissue containing the target;

detection means for detecting deflection of the target using the data from the imaging probe; and a control means for actuating the plurality of force applicators to apply forces on the soft tissue in response to a detected deflection of the target to move the target back in line with the path of the instrument.

2. The system of claim 1, wherein the imaging probe is mounted on a drive mechanism for moving the imaging probe in at least two dimensions with respect to the soft tissue; and wherein the control means is further for actuating the drive mechanism to move the imaging probe to maintain contact with the soft tissue and to track the target if the target moves out of a field of view of the imaging probe.

3. The system of claim 1, further comprising an instrument guidance device for fixing the path of the instrument.

4. The system of claim 3, wherein the instrument guidance device further has an instrument path sensor for measuring a characteristic of the path of the instrument; and wherein the control means utilizes the characteristic of the path of the instrument in actuating the plurality of force applicators to place the target in line with the path for insertion of the instrument.

5. The system of claim 2, wherein the control means includes a target manipulation system controller for controlling the manipulation system, an image acquisition system controller for controlling the image acquisition system, and a high level supervisory controller for coordinating the target manipulation system controller and the image acquisition system controller based on events.

6. The system of claim 5, wherein the control means further includes an interface between the high level supervisory controller, and the target manipulation system controller and the image acquisition system controller, the interface being for converting between continuous-time signals and sequences of symbols representing tasks.

7. The system of claim 6, wherein the high level supervisory controller further has a process monitoring module for monitoring event information received from the target manipulation system controller and the image acquisition system controller via the interface, and a decision making module for determining tasks to implement in response to the events, and sending control commands to the target manipulation system controller and the image acquisition system controller via the interface.

8. The system of claim 1, wherein the soft tissue is a breast.

9. A method for positioning a target located within soft tissue in a path of an instrument inserted into the soft tissue, comprising:

identifying the target using an image acquisition system including an imaging probe for obtaining data for generating an image of the soft tissue containing the target;

positioning the soft tissue containing the target in a manipulation system including a plurality of force applicators positioned around the soft tissue;

inserting the instrument into the soft tissue;

detecting deflection of the target using the data from the imaging probe; and actuating the plurality of force applicators to apply forces on the soft tissue in response to a detected deflection of the target to move the target back in line with the path of the instrument.

10. The method of claim 9, wherein the imaging probe is mounted on a drive mechanism for moving the imaging probe to maintain contact with the soft tissue and to track the target if the target moves out of a field of view of the imaging probe.

11. The method of claim 10, wherein moving the imaging probe to track the target further includes locating the target by actuating the drive mechanism.

12. The method of claim 11, further comprising:

detecting a loss of contact between the imaging probe and the soft tissue; and actuating the drive mechanism to reestablish contact between the imaging probe and the soft tissue.

13. The method of claim 9, wherein the soft tissue is a breast.

14. A device for positioning a target located within soft tissue, comprising:

an instrument configured to be inserted into the soft tissue along a path;

a manipulation system including a plurality of force applicators configured to be positioned around the soft tissue containing the target;

an image acquisition system including an imaging probe for obtaining data for generating an image of the soft tissue containing the target;

an instrument guidance device for fixing the path of the instrument;

detection means for detecting deflection of the target using the data from the imaging probe; and control means for actuating the plurality of force applicators to apply forces on the soft tissue in response to detecting a deflection of the target to move the target back in line with the path of the instrument.

15. The device of claim 14, wherein the image acquisition system further includes a drive mechanism for moving the imaging probe; and wherein the control means is further for actuating the drive mechanism to move the imaging probe to maintain contact with the soft tissue and to track the target if the target moves out of a field of view of the imaging probe.

16. The device of claim 15, wherein the control means includes a manipulation system controller for controlling the manipulation system, an image acquisition system controller for controlling the image acquisition system, and a high level supervisory controller for coordinating the manipulation system controller and the image acquisition system controller based on events.

17. The device of claim 16, wherein each of the plurality of force applicators includes an end effector positioned for engaging a surface of the soft tissue, an end effector actuator for effecting movement to the end effector, and an end effector position sensor for sensing a position of the end effector for use by the control means.

18. The device of claim 17, wherein the drive mechanism for moving the imaging probe moves the imaging probe in at least two dimensions and has an imaging probe position sensor for sensing a position of the imaging probe for use by the control means.

19. The device of claim 18, wherein the instrument guidance device has an instrument path sensor for sensing a characteristic of the path of the instrument for use by the control means.

20. The device of claim 19, wherein the soft tissue is a breast, wherein the imaging probe is an ultrasound imaging probe, and wherein the instrument is a biopsy needle.

* * * * *